(12) United States Patent
Kabumoto et al.

(10) Patent No.: US 8,483,475 B2
(45) Date of Patent: Jul. 9, 2013

(54) INSPECTION APPARATUS

(75) Inventors: Takashi Kabumoto, Shiga (JP); Osamu Hirose, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 512 days.

(21) Appl. No.: 12/676,344

(22) PCT Filed: Sep. 22, 2008

(86) PCT No.: PCT/JP2008/067110
§ 371 (c)(1),
(2), (4) Date: Mar. 3, 2010

(87) PCT Pub. No.: WO2009/041393
PCT Pub. Date: Apr. 2, 2009

(65) Prior Publication Data
US 2010/0202694 A1    Aug. 12, 2010

(30) Foreign Application Priority Data

Sep. 26, 2007  (JP) ................................ 2007-249899
Sep. 26, 2007  (JP) ................................ 2007-249905

(51) Int. Cl.
*G06K 9/00*    (2006.01)

(52) U.S. Cl.
USPC .......................................... 382/143; 382/141

(58) Field of Classification Search
USPC .................. 382/143, 100, 141, 149; 702/175;
378/51–58, 98.8–98.9; 250/308; 177/1, 210 R,
177/25.13
See application file for complete search history.

(56) References Cited

U.S. PATENT DOCUMENTS

| 5,585,603 A | 12/1996 | Vogeley, Jr. |
| 6,215,845 B1 | 4/2001 | Knigge |
| 2002/0019721 A1 | 2/2002 | Sakagami |
| 2002/0150206 A1* | 10/2002 | Sawada ........................... 378/57 |

FOREIGN PATENT DOCUMENTS

| EP | 1950527 A1 | 7/2008 |
| EP | 2042855 A1 | 4/2009 |
| JP | 2002-48623 A | 2/2002 |
| JP | 2002-228761 A | 8/2002 |
| JP | 2002-296022 A | 10/2002 |
| JP | 2002-310944 A | 10/2002 |
| JP | 2003-246307 A | 9/2003 |

(Continued)

OTHER PUBLICATIONS

Extended European Search Report of the corresponding European Application No. 08834624.2, dated Feb. 16, 2012.

*Primary Examiner* — Tri T Ton
(74) *Attorney, Agent, or Firm* — Global IP Counselors, LLP

(57) ABSTRACT

An inspection apparatus inspects a package group including a plurality of discrete packages that are successively connected in a chain. The inspection apparatus includes an irradiating component, a light receiving component, a generating component, an identifying component, an estimating component and a weight diagnosing component. The irradiating component is configured and arranged to irradiate inspection waves to the package group with the inspection waves being X-rays or terahertz waves. The identifying component is configured to identify a plurality of discrete package regions corresponding to the discrete packages from an inspection image generated by the generating component. The estimating component is configured to estimate one or more weight values respectively corresponding to one or more of the discrete package regions. The weight diagnosing component is configured to diagnose the package group as being abnormal in weight when any of the weight values falls outside a predetermined range.

10 Claims, 14 Drawing Sheets

FOREIGN PATENT DOCUMENTS

| | | |
|---|---|---|
| JP | 2003-291929 A | 10/2003 |
| JP | 2005-091015 A | 4/2005 |
| JP | 2005-127962 A | 5/2005 |
| JP | 2006-308467 A | 11/2006 |
| JP | 2006-329906 A | 12/2006 |
| JP | 2007-183200 A | 7/2007 |
| JP | 2007-232586 A | 9/2007 |
| WO | WO-2008/001785 A1 | 1/2008 |
| WO | WO-2009/012097 A1 | 1/2009 |
| WO | WO-2009/156468 A1 | 12/2009 |

* cited by examiner

INSPECTION APPARATUS

CROSS-REFERENCE TO RELATED APPLICATIONS

This national phase application claims priority to Japanese Patent Application No. 2007-249899 and Japanese Patent Application No. 2007-249905, both filed on Sep. 26, 2007. The entire disclosures of Japanese Patent Application Nos. 2007-249899 and 2007-249905 are hereby incorporated herein by reference.

TECHNICAL FIELD

The present invention relates to an inspection apparatus and particularly to an inspection apparatus that inspects a chain of successively connected packages including a plurality of discrete packages that are successively connected in a chain.

BACKGROUND ART

In a production line of products such as food products, in order to ensure that defective products are not shipped, sometimes weight inspection of the products is performed by a weight inspection apparatus or an X-ray inspection apparatus (e.g., see JP-A No. 2002-048623 and JP-A No. 2002-296022). Further, in a production line of products, sometimes inspection in regard to whether or not foreign matter is mixed into the products is performed by an X-ray inspection apparatus (e.g., see JP-A No. 2006-329906).

SUMMARY

However, in regard to a chain of successively connected packages, sometimes judgment of whether a product is normal or defective cannot be accurately performed by the aforementioned weight inspection or X-ray inspection. A chain of successively connected packages is a product including a plurality of discrete packages that are successively connected in a chain.

For example, a case will be considered here where the allowable error of the total weight of a chain of successively connected packages including ten discrete packages that weigh 10.0 g each and are successively connected in a chain is ±10%. In this case, as long as the total weight is between 90.0 g and 110.0 g, the chain of successively connected packages is handled as a normal product in the weight inspection.

But in a case where nine of the discrete packages weigh 10.5 g each and the one remaining discrete package weighs 6.0 g, the total weight becomes 100.5 g, so the chain of successively connected packages ends up being judged as normal in the conventional weight inspection. However, in regard to the discrete package that weighs 6.0 g, a weight error of −40% arises. Even though a chain of successively connected packages in which even one abnormal discrete package is present should be handled as a defective chain, the conventional weight inspection apparatus cannot detect an abnormality in weight at the level of the discrete packages. Further, in the conventional X-ray inspection apparatus also, the overall weight value is estimated, but an abnormality in weight at the level of the discrete packages is not detected.

Next, in the case where nine of the discrete packages weigh 10.5 g each, their total weight becomes 94.5 g, so even if the one remaining discrete package is an empty bag, the chain of successively connected packages ends up being judged as normal in the weight inspection.

Even though a chain of successively connected packages in which even one empty bag is present should be handled as a defective chain, it is difficult for the conventional weight inspection apparatus to detect that an empty bag is present. Further, in the conventional X-ray inspection apparatus also, the presence of foreign matter is detected, but the presence of an empty bag is not detected. For this reason, the current situation is such that the detection of empty bags is performed manually.

An object of the present invention is to provide an inspection apparatus that is capable of more accurately performing judgment of whether a chain of successively connected packages is normal or defective.

An inspection apparatus according to a first aspect of the invention includes an irradiating component, a light receiving component, a generating component, an identifying component, an estimating component and a weight diagnosing component and inspects a package group including a plurality of discrete packages that are successively connected in a chain. The irradiating component irradiates the package group with inspection waves that are X-rays or terahertz waves. The light receiving component receives the inspection waves from the irradiating component. The generating component generates an inspection image on the basis of the inspection waves that the light receiving component has received. The identifying component identifies discrete package regions from the inspection image. The discrete package regions are regions corresponding to the discrete packages of the package group. The estimating component estimates one or more weight values respectively corresponding to one or more of the discrete package regions. The weight diagnosing component diagnoses the package group as being abnormal in weight when any of the weight values falls outside a predetermined range.

This inspection apparatus is equipped with the function of performing weight estimation per discrete package of the package group. That is, in this inspection apparatus, even if the error of the total weight is within an allowable range, when even one discrete package with a weight outside the allowable range is present, it is possible to handle the package group as a defective chain that is abnormal in weight. Thus, in this inspection apparatus, it becomes possible to more accurately perform judgment of whether a package group is normal or defective.

An inspection apparatus according to a second aspect of the invention is the inspection apparatus according to the first aspect of the invention, wherein the identifying component recognizes content regions as the discrete package regions. The content regions are regions corresponding to contents of the discrete packages.

This inspection apparatus performs weight estimation with respect to the content regions on the inspection image. The content regions may be understood to be regions where contents are actually present or regions for packaging contents (that is, regions where contents can be present). That is, in this inspection apparatus, regions where contents cannot be present on the inspection image (such as seal regions corresponding to seal sites of the package group) are not made into the target of weight estimation, so the weight values that are estimated have little error and more accurately reflect amounts of contents.

Incidentally, in a package group such as a three-side seal type where seals are administered to three end sides of the package group, the percentage of the sites where contents cannot be present in the entire package group becomes large. Consequently, in the inspection of such a package group, excluding regions where contents cannot be present from the target of weight estimation is particularly useful from the standpoint of error reduction.

An inspection apparatus according to a third aspect of the invention is the inspection apparatus according to the second aspect of the invention, wherein the identifying component identifies seal regions from the inspection image and identifies the content regions in regions other than the seal regions of the inspection image. The seal regions are regions corresponding to seal sites of the package group.

This inspection apparatus first identifies the seal regions from the inspection image and next identifies the content regions from the remaining regions excluding the seal regions of the inspection image. It is anticipated that, in contrast to a case where the inspection waves are transmitted through packaging spaces in the discrete packages where the contents can be unevenly distributed, the extent of attenuation of the inspection waves that are transmitted through the seal sites will become generally constant. That is, usually, identifying the seal regions with the inspection waves that have been transmitted through the seal sites is more reliable than identifying the content regions with the inspection waves that have been transmitted through the packaging spaces in the discrete packages. Consequently, in this inspection apparatus, the content regions can be extracted more precisely by first identifying the seal regions.

An inspection apparatus according to a fourth aspect of the invention is the inspection apparatus according to any of the first aspect to the third aspect of the invention, wherein the identifying component extracts the discrete package regions by performing image processing with respect to the inspection image.

This inspection apparatus can extract the discrete package regions by image-processing the inspection image showing the package group.

An inspection apparatus according to a fifth aspect of the invention is the inspection apparatus according to the first aspect or the second aspect of the invention, wherein the identifying component identifies the discrete package regions from the inspection image on the basis of a parameter set beforehand.

In this inspection apparatus, a parameter for identifying the discrete package regions is set beforehand. Thus, the inspection apparatus can easily identify the discrete package regions on the inspection image.

An inspection apparatus according to a sixth aspect of the invention is the inspection apparatus according to any of the first aspect to the fifth aspect of the invention and further comprises a foreign matter inspecting component. The foreign matter inspecting component performs foreign matter inspection with respect to the package group on the basis of the inspection image.

This inspection apparatus performs foreign matter inspection of the entire package group together with weight inspection per discrete package. By performing foreign matter inspection of the entire package group and weight inspection per discrete package with one apparatus in this manner, the footprint of the production line of the package group can be reduced and costs for constructing the production line can be reduced.

An inspection apparatus according to a seventh aspect of the invention is the inspection apparatus according to the sixth aspect of the invention and further comprises an integrated diagnosing component. The integrated diagnosing component diagnoses the package group as being abnormal at least one of when the weight diagnosing component has diagnosed the package group as being abnormal in weight and when the foreign matter inspecting component has diagnosed that foreign matter is mixed into the package group.

This inspection apparatus diagnoses the package group as being abnormal when an abnormality is detected in at least one of the weight inspection per discrete package and the foreign matter inspection of the entire package group. Thus, in this inspection apparatus, the processing burden on the inspection is alleviated.

An inspection apparatus according to an eighth aspect of the invention is the inspection apparatus according to any of the first aspect to the seventh aspect of the invention, wherein the weight diagnosing component sequentially diagnoses abnormality in each of the discrete packages of the package group as the estimating component completes estimation of the weight value of each of the discrete package regions, and the estimating component stops estimating the weight values of remaining ones of the discrete package regions at a point in time when one of the discrete packages of the package group is diagnosed by the weight diagnosing component as being abnormal in weight.

In this inspection apparatus, when an abnormality in weight is detected with respect to even one of the discrete packages, the weight inspection ends without performing the weight estimation with respect to the discrete package regions where the estimation has not finished at the time of that detection. Thus, the processing burden on the weight inspection is alleviated.

An inspection apparatus according to a ninth aspect of the invention is the inspection apparatus according to any of the first aspect to the eighth aspect of the invention, wherein the weight diagnosing component determines whether or not an empty bag is included in the package group on the basis of the weight values.

This inspection apparatus judges that an empty bag is included in the package group when a weight value that has been estimated with respect to a given discrete package region becomes zero or a value close to zero. Thus, in this inspection apparatus, a package group in which an empty bag is present can be handled as a defective chain.

An inspection apparatus according to a tenth aspect of the invention includes an irradiating component, a light receiving component and an empty bag inspecting component and inspects a package group including a plurality of discrete packages that are successively connected in a chain. The irradiating component irradiates the package group with inspection waves that are X-rays or terahertz waves. The light receiving component receives the inspection waves from the irradiating component. The empty bag inspecting component inspects whether or not at least one empty bag is included in the package group on the basis of output values of the light receiving component.

This inspection apparatus is equipped with the function of inspecting whether or not an empty bag is included in the package group. That is, in this inspection apparatus, even if the error of the total weight is within an allowable range, when even one empty bag is present, it is possible to handle the package group as a defective chain. It will be noted that, in the present application, "empty" includes not only a state where there are no contents at all in a discrete package but also a state where there is only a minute amount of contents in a discrete package. Thus, in this inspection apparatus, it becomes possible to more accurately perform judgment of whether a package group is normal or defective.

An inspection apparatus according to an eleventh aspect of the invention is the inspection apparatus according to the tenth aspect of the invention, wherein the empty bag inspecting component performs the empty bag inspection on the basis of an emergent pattern of at least one of a light state and a dark state. The light state is a state where values based on the output values of the light receiving component exceed a predetermined value. The dark state is a state where values based on the output values of the light receiving component fall below the predetermined value This inspection apparatus judges an emergent pattern of at least one of a light state and a dark state and performs the empty bag inspection on the basis of the emergent pattern. The light state corresponds to a state where the amount of inspection waves that have passed through the package group and reached the light receiving component is large, and the dark state corresponds to a state where the amount of inspection waves that have passed through the package group and reached the light receiving component is small. In other words, the light state is a state that is judged on the basis of the inspection waves that have passed mainly through the packaging material of the package group, and the dark state is a state that is judged on the basis of the inspection waves that have passed mainly through the contents of the package group. That is, this inspection apparatus can judge an emergent pattern of masses of contents of the package group indirectly by judging an emergent pattern of at least one of the light state and the dark state; thus, this inspection apparatus can perform the empty bag inspection.

An inspection apparatus according to a twelfth aspect of the invention is the inspection apparatus according to the eleventh aspect of the invention, wherein the empty bag inspecting component performs the inspection on the basis of a first number of times. The first number of times is a number of times that the values switch from the light state to the dark state.

This inspection apparatus judges the number of times that the values have switched from the light state to the dark state and performs the empty bag inspection on the basis of this number of times. That is, this inspection apparatus can judge the number of masses of contents of the package group indirectly by judging the number of times that the values have switched from the light state to the dark state; thus, this inspection apparatus can perform the empty bag inspection.

An inspection apparatus according to a thirteenth aspect of the invention is the inspection apparatus according to the eleventh aspect or the twelfth aspect of the invention, wherein the empty bag inspecting component performs the inspection on the basis of a second number of times. The second number of times is a number of times that the values switch from the dark state to the light state.

This inspection apparatus judges the number of times that the values have switched from the dark state to the light state and performs the empty bag inspection on the basis of this number of times. That is, this inspection apparatus can judge the number of masses of contents of the package group indirectly by judging the number of times that the values have switched from the dark state to the light state; thus, this inspection apparatus can perform the empty bag inspection.

An inspection apparatus according to a fourteenth aspect of the invention is the inspection apparatus according to the eleventh aspect of the invention, wherein the empty bag inspecting component performs the inspection on the basis of a span where the light state is continuous.

This inspection apparatus judges spans of the light state and performs the empty bag inspection on the basis of the spans. That is, this inspection apparatus judges spans where sites where there are no contents are continuous indirectly by judging spans where the light state is continuous; thus, this inspection apparatus can perform the empty bag inspection.

An inspection apparatus according to a fifteenth aspect of the invention is the inspection apparatus according to the tenth aspect of the invention, wherein the empty bag inspecting component performs the inspection on the basis of an inspection image that has been generated on the basis of the inspection waves that the light receiving component has received.

This inspection apparatus performs the empty bag inspection by administering image processing to the inspection image showing the package group. Thus, this inspection apparatus can perform the empty bag inspection while effectively utilizing the function with which an inspection apparatus is inherently equipped.

An inspection apparatus according to a sixteenth aspect of the invention is the inspection apparatus according to the fifteenth aspect of the invention, wherein the empty bag inspecting component extracts content regions from the inspection image and performs the inspection on the basis of the number of the content regions. The content regions are regions corresponding to contents of the discrete packages.

This inspection apparatus extracts the content regions from the inspection image showing the package group and judges the number of the content regions, whereby this inspection apparatus can perform the empty bag inspection on the basis of that number.

An inspection apparatus according to a seventeenth aspect of the invention is the inspection apparatus according to the fifteenth aspect of the invention, wherein the empty bag inspecting component extracts content regions corresponding to contents of the discrete packages from the inspection image and performs the inspection on the basis of intervals between the content regions.

This inspection apparatus extracts the content regions from the inspection image showing the package group and judges the intervals at which the content regions appear on the inspection image, whereby this inspection apparatus can perform the empty bag inspection on the basis of those intervals.

An inspection apparatus according to an eighteenth aspect of the invention is the inspection apparatus according to any of the fifteenth aspect to the seventeenth aspect of the invention and further comprises a foreign matter inspecting component. The foreign matter inspecting component performs inspection of foreign matter on the basis of the inspection image.

This inspection apparatus performs foreign matter inspection together with the empty bag inspection. By performing the foreign matter inspection and the empty bag inspection with one apparatus in this manner, the footprint of the production line of the package group can be reduced and costs for constructing the production line can be reduced.

An inspection apparatus according to a nineteenth aspect of the invention is the inspection apparatus according to the eighteenth aspect of the invention, wherein the empty bag inspecting component and the foreign matter inspecting component stop inspection of the package group when an abnormality has been detected in the inspections by either one of the empty bag inspecting component and the foreign matter inspecting component.

In this inspection apparatus, for example, when the presence of an empty bag is detected in the empty bag inspection, the foreign matter inspection unfinished at the time of that detection ends as is. And when the presence of foreign matter is detected in the foreign matter inspection, the empty bag inspection unfinished at the time of that detection ends as is. Thus, the processing burden on the inspection is alleviated.

According to the inspection apparatus according to the above described aspects, it becomes possible to more accurately perform judgment of whether a package group is normal or defective.

DETAIL DESCRIPTION OF THE EMBODIMENTS

Below, X-ray inspection apparatus 10, 110, 210, 310 and 410 according to first, second, third, fourth and fifth embodiments of the present invention will be described with reference to the drawings.

First Embodiment

Figure 1:
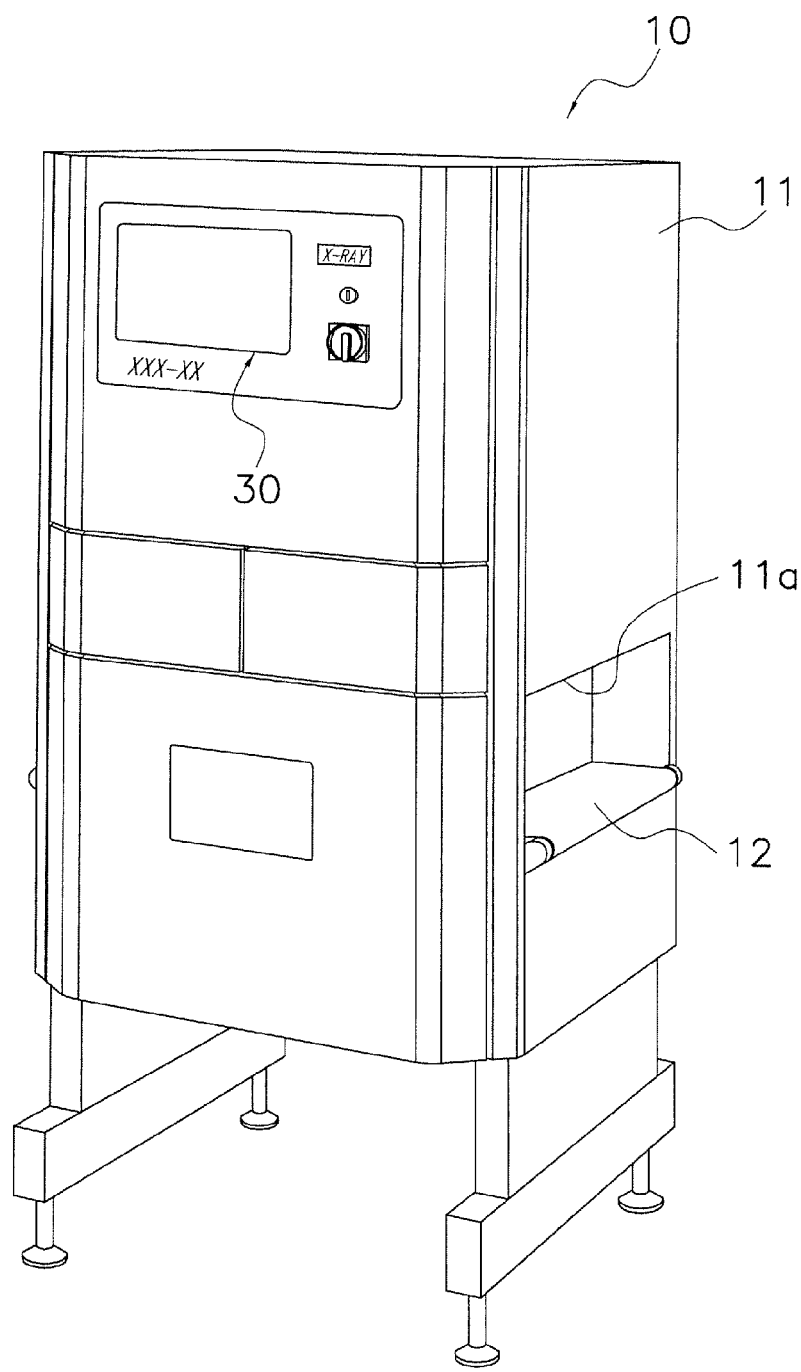
FIG. 1 is an external perspective diagram of an X-ray inspection apparatus according to a first embodiment of the present invention.

FIG. 1 shows the exterior of the X-ray inspection apparatus 10 according to the first embodiment of the present invention. The X-ray inspection apparatus 10 is one apparatus that is incorporated in a production line of products G such as food products and performs quality inspection of products G, and the X-ray inspection apparatus 10 is an apparatus that performs judgment of whether the products G are normal or defective by irradiating the products G that are continuously conveyed with X-rays.

Figure 4:
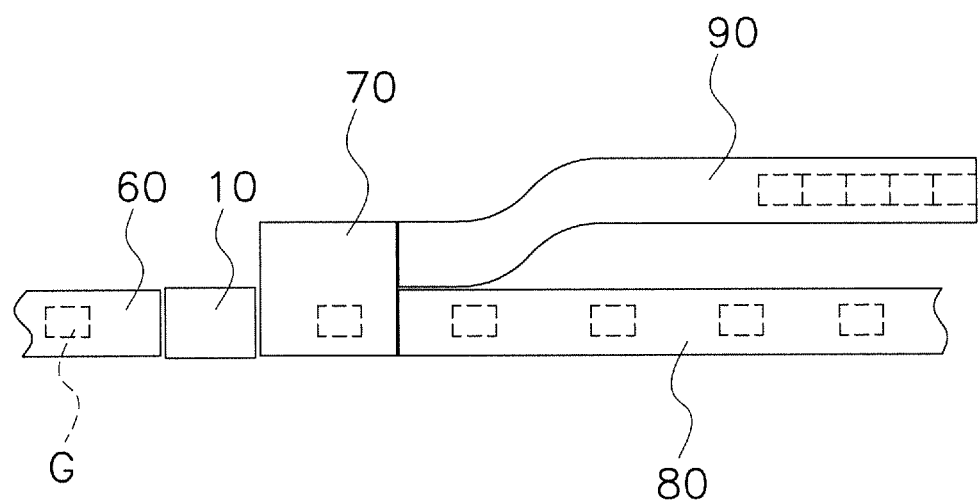
FIG. 4 is a configuration diagram of the surroundings of the X-ray inspection apparatus.

The products G, which are objects of inspection, are conveyed by an upstream conveyor 60 to the X-ray inspection apparatus 10 as shown in FIG. 4. The products G are classified into normal products and defective products in the X-ray inspection apparatus 10. The inspection results of the X-ray inspection apparatus 10 are sent to a sorting mechanism 70 that is disposed on a downstream side of the X-ray inspection apparatus 10. The sorting mechanism 70 sends products G that have been judged to be normal products in the X-ray inspection apparatus 10 to a regular line conveyor 80 and sends products G that have been judged to be defective products in the X-ray inspection apparatus 10 to a defective product storage conveyor 90.

Configuration of X-Ray Inspection Apparatus

Figure 2:
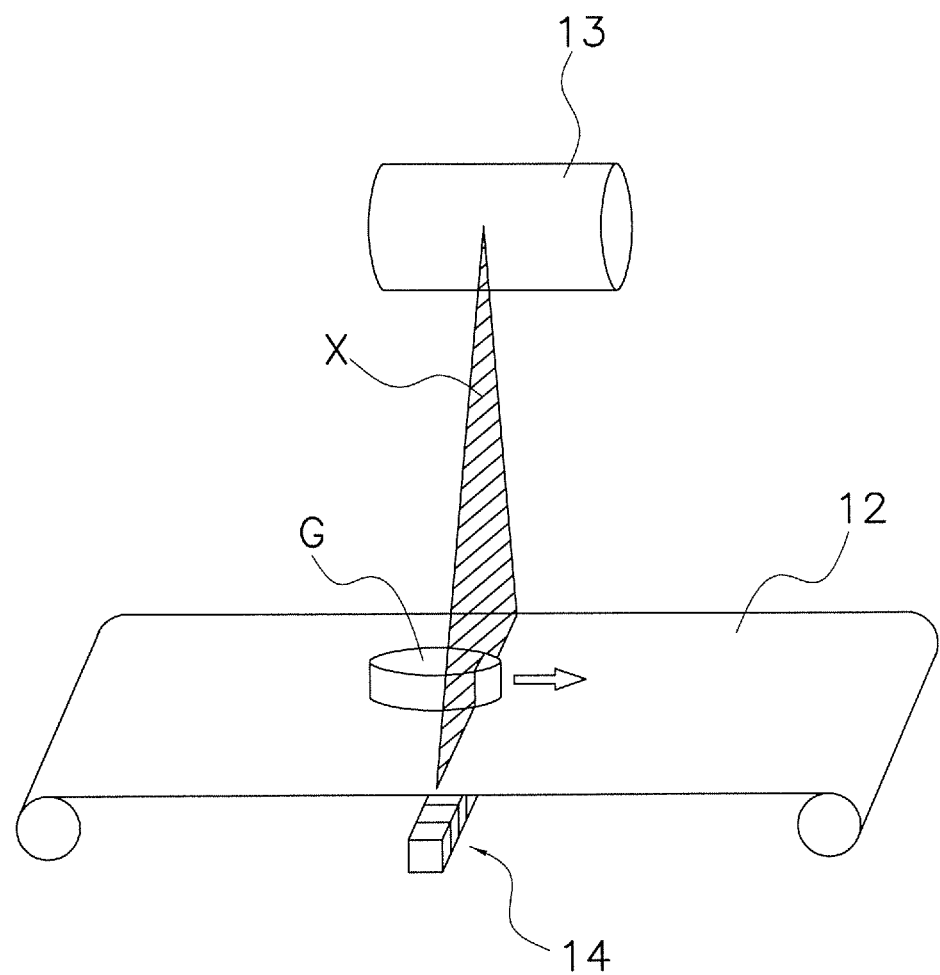
FIG. 2 is a configuration diagram of the inside of a shield box of the X-ray inspection apparatus.
Figure 5:
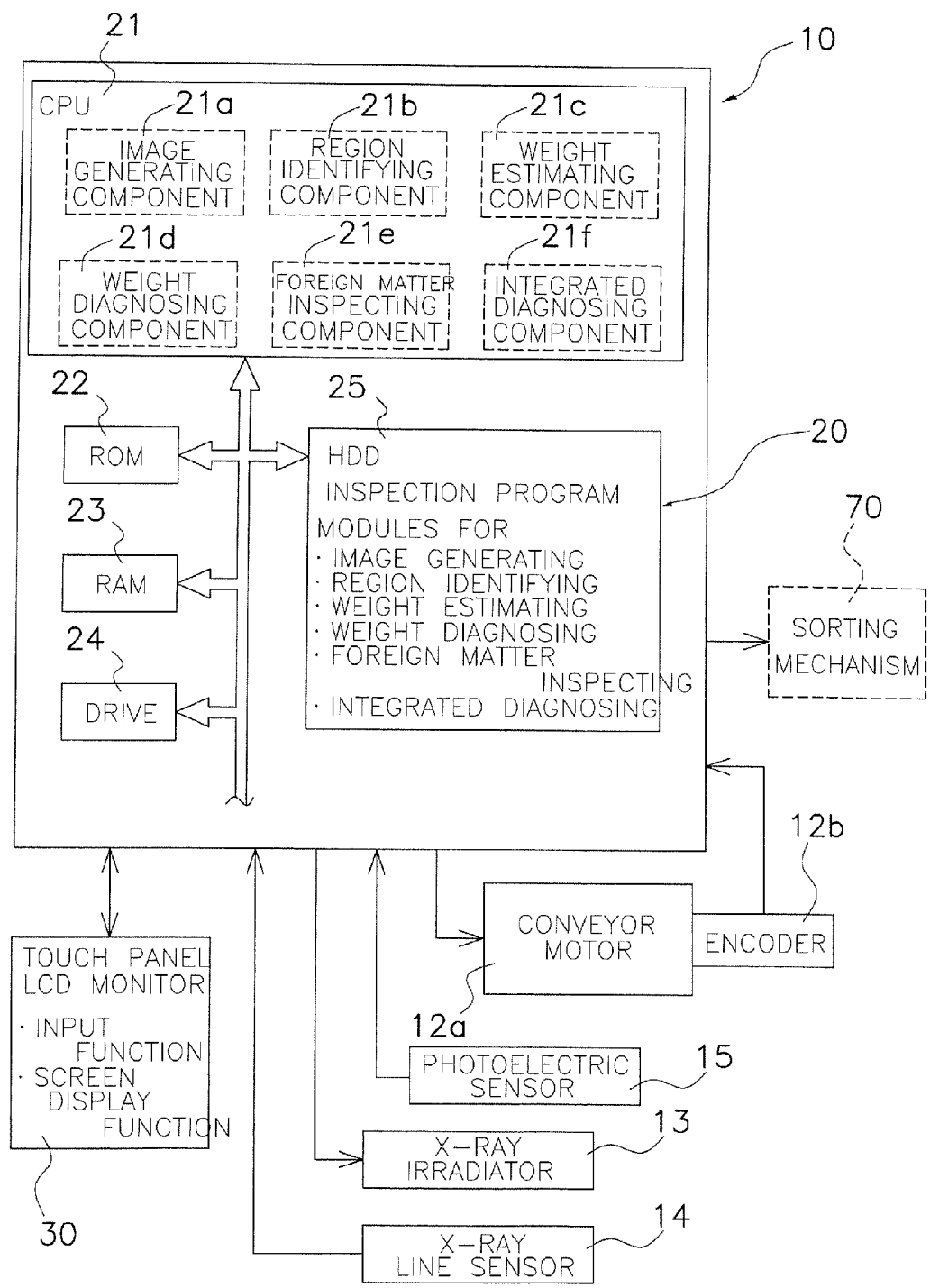
FIG. 5 is a block configuration diagram of a control computer according to the first embodiment of the present invention.

As shown in FIG. 1, FIG. 2 and FIG. 5, the X-ray inspection apparatus 10 is mainly configured by a shield box 11, a conveyor 12, an X-ray irradiator 13, an X-ray line sensor 14, a monitor 30 disposed with a touch panel function, and a control computer 20.

Shield Box

In both side surfaces of the shield box 11, there are formed openings 11a for allowing the products G to be conveyed into and out of the shield box 11. The openings 11a are blocked off by shielding curtains (not shown) in order to prevent leakage of X-rays to the outside of the shield box 11. The shielding curtains are formed by a rubber that includes lead and are configured such that they are pushed aside by the products G when the products G pass through the openings 11a.

Additionally, inside the shield box 11, there are housed the conveyor 12, the X-ray irradiator 13, the X-ray line sensor 14 and the control computer 20. Further, the monitor 30, a keyhole, a power switch and the like are disposed on the upper portion of the front surface of the shield box 11.

Conveyor

The conveyor 12 conveys the products G inside the shield box 11 and is, as shown in FIG. 1, disposed so as to penetrate the openings 11a formed in both side surfaces of the shield box 11. Additionally, the conveyor 12 includes an endless belt that is rotated by a drive roller that is driven by a conveyor motor 12a (see FIG. 5), and the conveyor 12 conveys the products G that have been placed on the belt.

The conveyance speed of the conveyor 12 is finely controlled by inverter control of the conveyor motor 12a controlled by the control computer 20 such that the conveyance speed becomes equal to a setting speed that an operator has inputted. Further, an encoder 12b (see FIG. 5) that detects the conveyance speed of the conveyor 12 and sends the detection result to the control computer 20 is attached to the conveyor motor 12a.

X-Ray Irradiator

The X-ray irradiator 13 is, as shown in FIG. 2, disposed above the conveyor 12 and irradiates with X-rays in a fan-shaped irradiated range X toward the X-ray line sensor 14 located below the conveyor 12.

X-Ray Line Sensor

Figure 3:
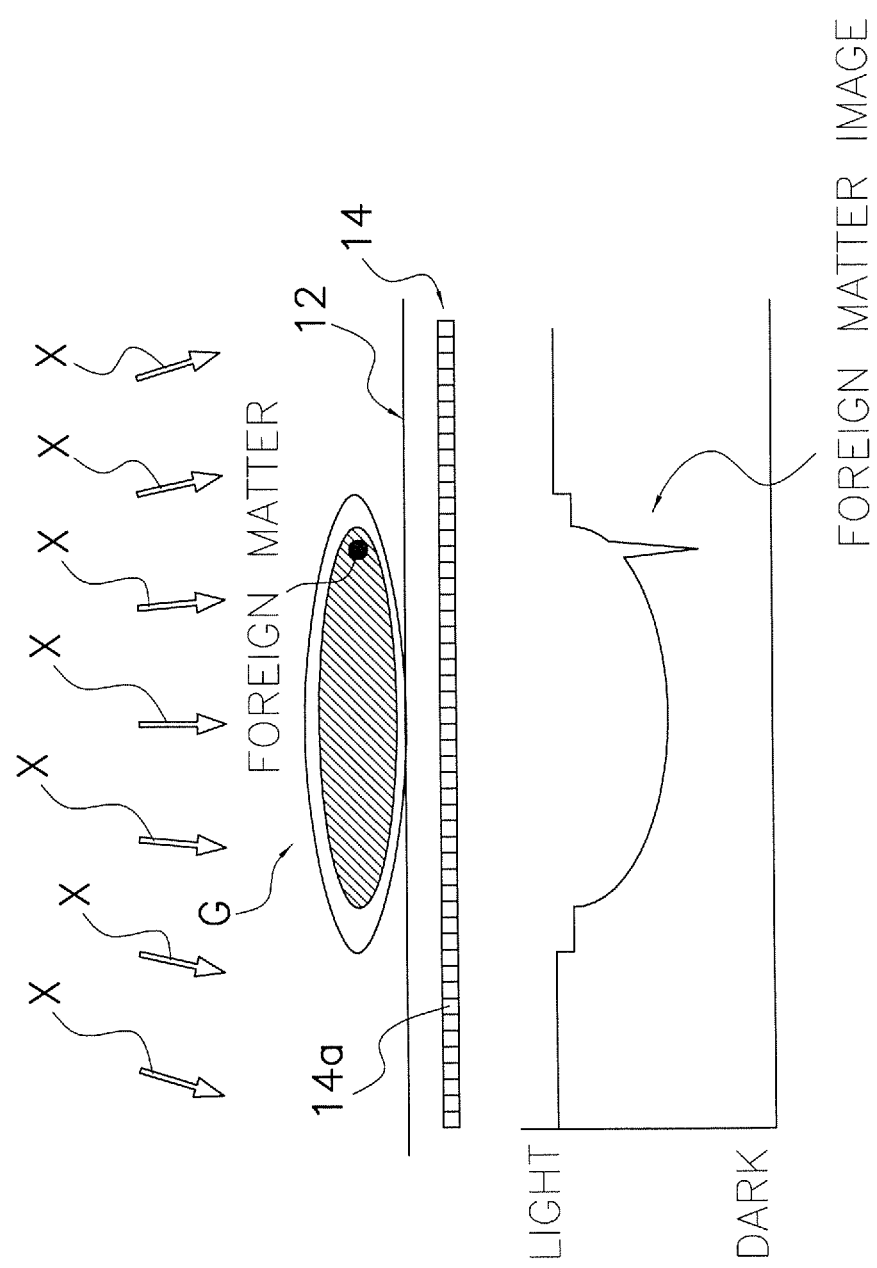
FIG. 3 is a schematic diagram showing the principle of X-ray inspection.

The X-ray line sensor 14 is, as shown in FIG. 3, disposed below the conveyor 12 and is mainly configured by numerous pixel sensors 14a. The pixel sensors 14a are horizontally arranged in a straight line in a direction orthogonal to the conveyance direction of the conveyor 12. Further, each of the pixel sensors 14a detects the X-rays that have been transmitted through the products G and the conveyor 12 and outputs an X-ray see-through image signal. The X-ray see-through image signals represent the lightness (concentration) of the X-rays.

Monitor

The monitor 30 is a full-dot liquid crystal display and displays screens prompting the operator to input an inspection parameter or the like that becomes necessary during inspection. Further, the monitor 30 also includes a touch panel function and receives input of the inspection parameter or the like from the operator.

Control Computer

The control computer 20 is, as shown in FIG. 5, equipped with a central processing unit (CPU) 21, a read-only memory (ROM) 22, a random access memory (RAM) 23, a hard disk (HDD) 25, and a drive 24 for inserting storage media and the like.

In the CPU 21, various programs stored in the ROM 22 and in the HDD 25 are executed. The inspection parameter and inspection results are saved and accumulated in the HDD 25. The inspection parameter can be set and altered by input from the operator using the touch panel function of the monitor 30. The operator can set these data to be saved and accumulated not only in the HDD 25 but also in a storage medium that has been inserted into the drive 24.

Moreover, the control computer 20 is also equipped with a display control circuit (not shown) that controls the display of data on the monitor 30, a key input circuit (not shown) that imports key input data that have been inputted by the operator via the touch panel of the monitor 30, and a communication port (not shown) that enables connection to an external device such as a printer (not shown) and a network such as a LAN.

Additionally, the components 21 to 25 of the control computer 20 are interconnected via a bus line such as an address bus or a data bus.

Further, the control computer 20 is connected to the conveyor motor 12a, the encoder 12b, a photoelectric sensor 15, the X-ray irradiator 13, the X-ray line sensor 14 and the like. The photoelectric sensor 15 is a synchronous sensor for sensing the timings when the products G that are objects of inspection pass through the fan-shaped X-ray irradiated range X (see FIG. 2) and is mainly configured by a phototransmitter and a photoreceiver that are disposed so as to sandwich the conveyor 12.

Judgment of Whether Products are Normal or Defective by Control Computer

In the HDD 25 of the control computer 20, there is stored an inspection program that includes an image generating module, a region identifying module, a weight estimating module, a weight diagnosing module, a foreign matter inspecting module and an integrated diagnosing module. By reading and executing these program modules, the CPU 21 of the control computer 20 operates as an image generating component 21a, a region identifying component 21b, a weight estimating component 21c, a weight diagnosing component 21d, a foreign matter inspecting component 21e and an integrated diagnosing component 21f (see FIG. 5).

The image generating component 21a generates an X-ray image of the products G on the basis of the X-ray see-through image signals outputted from the X-ray line sensor 14.

The region identifying component 21b, the weight estimating component 21c and the weight diagnosing component 21d carry a weight inspecting function that is used only when the products G that become objects of inspection are a chain of successively connected packages (a package group), and when the products G that become objects of inspection are not a chain of successively connected packages, the weight inspecting function is set to OFF by the operator.

When the weight inspecting function is set to ON, the region identifying component 21b identifies discrete package regions corresponding to discrete packages of a chain of successively connected packages from the X-ray image that has been generated by the image generating component 21a and which shows the products G that are a chain of successively connected packages. The weight estimating component 21c estimates weight values of contents packaged in each of the discrete packages by administering image processing with respect to each of the discrete package regions that have been identified by the region identifying component 21b. The weight diagnosing component 21d checks whether or not the weight values that have been calculated by the weight estimating component 21c fall within a predetermined range, and when even one weight value that falls outside the predetermined range is present, the weight diagnosing component 21d judges that product G to be abnormal.

The foreign matter inspecting component 21e inspects whether or not foreign matter is included in the products G by administering image processing with respect to the X-ray image that has been generated by the image generating component 21a. When foreign matter is included, the foreign matter inspecting component 21e judges that product G to be abnormal.

The integrated diagnosing component 21f diagnoses a product G in which an abnormality has been detected by at least one of the weight diagnosing component 21d and the foreign matter inspecting component 21e as being a defective product and diagnoses a product G in which no abnormality has been detected by either the weight diagnosing component 21d or the foreign matter inspecting component 21e as being a normal product. The operator may also add a new inspecting module so that it is also possible for the integrated diagnosing component 21f to perform other inspection with respect to the products G. In this case, the integrated diagnosing component 21f diagnoses only a product G that has been judged to be normal in all of the inspections as being a normal product.

The diagnostic results of the integrated diagnosing component 21f are sent to the sorting mechanism 70. Then, the sorting mechanism 70 judges whether it should sort the products G onto the regular line conveyor 80 or the defective product storage conveyor 90 on the basis of the diagnostic results.

Below, details of the operation of the image generating component 21a, the region identifying component 21b, the weight estimating component 21c, the weight diagnosing component 21d, the foreign matter inspecting component 21e and the integrated diagnosing component 21f will be described.

Image Generating Component

The image generating component 21a acquires, in fine time intervals, the X-ray see-through image signals outputted from each of the pixel sensors 14a of the X-ray line sensor 14 when the products G pass through the fan-shaped X-ray irradiated range X (see FIG. 2) and generates an X-ray image of the products G on the basis of the acquired X-ray see-through image signals. The timings when the products G pass through the fan-shaped X-ray irradiated range X are judged by signals from the photoelectric sensor 15. That is, the image generating component 21a generates an X-ray image showing the products G by joining together, in a matrix in a time series, data per fine time interval relating to the lightness of the X-rays obtained from each of the pixel sensors 14a of the X-ray line sensor 14.

Below, a case where a chain of successively connected packages M shown in FIG. 6(a) serves as the object of inspection will be taken as an example and described. The chain of successively connected packages M includes six bags N1, N2, . . . , N6 that are successively connected in order in a chain, and the bags N1, N2, . . . , N6 are manufactured such that they all have the same shape. The chain of successively connected packages M is conveyed by the conveyor 12 such that the bag N1 is at the front and the bag N6 is at the rear. Each of the bags N1, N2, . . . , N6 is a so-called pillow bag. Transverse seal sites S1 are formed on both ends of each of the bags N1, N2, . . . , N6 in the conveyance direction of the conveyor 12, and a vertical seal site S2 that extends in the conveyance direction is formed on the surface of each of the bags N1, N2, . . . , N6 that faces the conveyance surface of the conveyor 12. That is, the chain of successively connected packages M is a single long and narrow bag overall in which plural spaces corresponding to each of the bags N1, N2, . . . , N6 are formed by the transverse seal sites S1 administered at predetermined intervals in the longitudinal direction of the chain of successively connected packages M. Additionally, contents are packaged in the spaces inside the bags N1, N2, . . . , N6. Further, the transverse seal site S1 on the rear side of each preceding bag and the transverse seal site S1 on the front side of each following bag are integrally heat-sealed and formed, and in the center thereof, there is formed a perforation that runs in the short direction and enables both bags to be separated.

Figure 6:
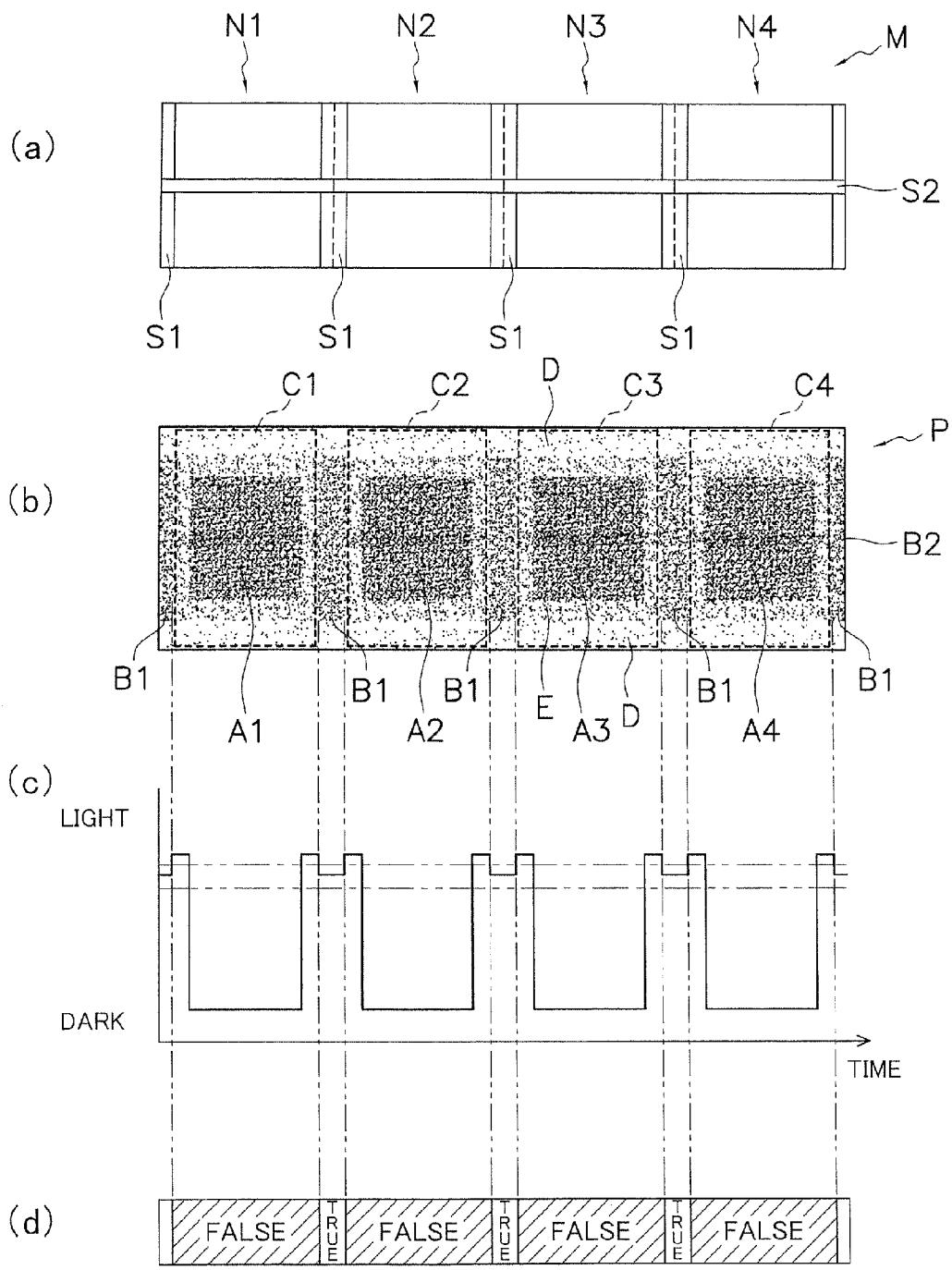
FIG. 6(a) is a diagram showing a chain of successively connected packages.
FIG. 6(b) is a diagram showing an X-ray image of the chain of successively connected packages.
FIG. 6(c) is a diagram showing the result of representative value decision processing.
FIG. 6(d) is a diagram showing the result of true/false determination processing according to the first embodiment.

FIG. 6(b) shows an X-ray image P of the chain of successively connected packages M shown in FIG. 6(a). It will be noted that, for the sake of brevity, FIG. 6(a) to FIG. 6(d) show only the bags N1 to N4 of the entire chain of successively connected packages M. On the X-ray image P, regions A1 to A4 that appear the darkest represent the contents inside the bags N1 to N4, regions B1 represent the transverse seal sites S1, and a region B2 represents the vertical seal site S2. A region D that appears the lightest represents the background of the chain of successively connected packages M, and regions E that appear lighter than the regions B1 and B2 and darker than the region D represent vacant portions of the bags N1 to N4 where there are no contents. It is thought that the reason why the regions B1 corresponding to the transverse seal sites S1 appear darker on the X-ray image P than the regions E corresponding to sites that are not sealed, even though both regions are sites where the same number of layers of packaging material overlap, is because the density of the transverse seal sites S1 is higher because of heat shrinkage than that of sites that are not sealed. Further, when processing is administered to the seal sites S1 and S2 such that they become jagged, the seal sites S1 and S2 appear darker on the X-ray image P because of overlapping of the packaging material in comparison to when this processing is not administered.

Region Identifying Component

Like the image generating component 21a, the region identifying component 21b acquires, in fine time intervals, the X-ray see-through image signals from each of the pixel sensors 14a of the X-ray line sensor 14. Additionally, the region identifying component 21b calculates an average value of concentration values of the X-rays that correspond to the number of the pixel sensors 14a and have been outputted at the same timing from the numerous pixel sensors 14a and uses the calculated value as a representative value of the concentration values of the X-rays in that timing. Additionally, the region identifying component 21b checks whether or not the representative value falls within a predetermined range, regards a case where the representative value falls within the range as being "true", and regards a case where the representative value does not fall within the range as being "false". As the range of the representative value that is used in this true/false determination processing, a possible range of representative values when the transverse seal sites S1 pass through the irradiated region X is set. It is thought that the contents will not overlap the transverse seal sites S1 even though the contents can be unevenly distributed inside the packaging spaces in the chain of successively connected packages M, so it is anticipated that the extent of attenuation of the X-rays that have been transmitted through the transverse seal sites S1 will become generally constant. Consequently, it is possible to precisely set beforehand a possible range of representative values when the transverse seal sites S1 have passed through the irradiated region X.

The region identifying component 21b repeats the representative value decision processing and the true/false determination processing each time it receives a data set of one group of concentration values (X-ray see-through image signals whose number corresponds to the number of the pixel sensors 14a outputted at substantially the same timing from the X-ray line sensor 14). Then, when a "true" state continues for a predetermined length corresponding to the width of the transverse seal site S1, the region identifying component 21b detects the presence of the transverse seal site S1.

FIG. 6(c) shows time series data of the representative values calculated on the basis of the X-ray see-through image signals when the bags N1 to N4 have passed through the X-ray irradiated range X. In this case, the true/false determination processing results in what is shown in FIG. 6(d).

Next, the region identifying component 21b overlays the result of the true/false determination processing on the X-ray image P that has been generated by the image generating component 21a and identifies the regions corresponding to "false" on the X-ray image P as discrete package regions C1, C2, . . . , C6. The discrete package regions C1, C2, . . . , C6 are, in contrast to the regions corresponding to "true" (including the regions B1), regions where contents can be present.

Weight Estimating Component

The weight estimating component 21c performs weight estimation with respect to each of the discrete package regions C1, C2, . . . , C6 that have been identified by the region identifying component 21b. This weight estimation processing is performed on the basis of the following principle utilizing the property that the thicker the matter is in the direction in which it is irradiated with the X-rays the darker it appears on the X-ray image P.

A lightness I of pixels showing matter with a thickness t on the X-ray image P is expressed by the following expression (1) when $I_0$ represents the lightness of pixels included in a region where the matter is not present.

$$I/I_0 = e^{-\mu t} \qquad (1)$$

Here, $\mu$ is a linear absorption coefficient that is determined depending on the energy of the X rays and the type of the matter. When expression (1) is solved in regard to the thickness t of the matter, the following expression (2) is obtained.

$$t = -1/\mu \times \ln(I/I_0) \qquad (2)$$

Further, the weight value of a tiny site of contents is proportional to the thickness of that tiny site. Consequently, a weight value m of a tiny site of contents appearing in a pixel of the lightness I is calculated approximately by the following expression (3) using an appropriate constant $\alpha$.

$$m = -\alpha \ln(I/I_0) \qquad (3)$$

The weight estimating component 21c estimates the weight values of all of the contents inside each of the bags N1, N2, . . . , N6 by adding the calculated weight values m corresponding to all of the pixels that configure each of the discrete package regions C1, C2, . . . , C6.

Weight Diagnosing Component

The weight diagnosing component 21d checks whether or not the weight values of all of the contents inside each of the bags N1, N2, . . . , N6 fall within a predetermined range. When all of the weight values fall within the range, the weight diagnosing component 21d diagnoses the chain of successively connected packages M as being normal, and when even any one weight value does not fall within the range, the weight diagnosing component 21d diagnoses the chain of successively connected packages M as being abnormal in weight. The weight diagnosing component 21d can also determine that an empty bag is included in the chain of successively connected packages M when the weight value is smaller than a prescribed minute weight.

Processing by the weight diagnosing component 21d is executed in parallel with processing by the weight estimating component 21c with initiation of processing by the weight diagnosing component being later than initiation of processing by the weight estimating component 21. In other words, processing by the weight estimating component 21c and processing by the weight diagnosing component 21d are subsequently executed with respect to each of the discrete package regions C1, C2, . . . , C6 in this order. When the weight diagnosing component 21d detects an abnormality in weight in regard to any one of the bags N1, N2, . . . , N5, the weight diagnosing component 21d diagnoses the chain of successively connected packages M as being abnormal in weight and immediately causes the weight estimation processing by the weight estimating component 21c with respect to the remaining discrete package regions C2, C3, . . . , C6 unfinished at that point in time to end. This is because the weight diagnosing component 21d can conclude that the chain of successively connected packages M is abnormal in weight, regardless of the weight values of the remaining bags N2, N3, . . . , N6, because a chain of successively connected packages M that includes even one bag N1, N2, . . . , N6 that is abnormal in weight cannot be shipped.

Foreign Matter Inspecting Component

The foreign matter inspecting component 21e detects foreign matter included in the chain of successively connected packages M by administering binary processing with respect to the X-ray image P of the chain of successively connected packages M that has been generated by the image generating component 21a. More specifically, when a region that appears darker than a threshold value set beforehand is present on the X-ray image P of the chain of successively connected packages M, the foreign matter inspecting component 21e judges that foreign matter is mixed into the chain of successively connected packages M and judges the chain of successively connected packages M to be abnormal.

Further, the foreign matter inspecting component 21e is also capable of setting a mask on the X-ray image P. The mask is, for example, set with respect to the regions B1 corresponding to the transverse seal sites S1 of the chain of successively connected packages M and the region D corresponding to the background.

Integrated Diagnosing Component

When the weight diagnosing component 21d and the foreign matter inspecting component 21e judge the chain of successively connected packages M to be abnormal, they immediately send signals indicating this to the integrated diagnosing component 21f. When the integrated diagnosing component 21f receives this signal from the weight diagnosing component 21d, the integrated diagnosing component 21f diagnoses the chain of successively connected packages M as being a defective chain and immediately causes inspection by the foreign matter inspecting component 21e to end. When the integrated diagnosing component 21f receives this signal from the foreign matter inspecting component 21e, the integrated diagnosing component 21f diagnoses the chain of successively connected packages M as being a defective chain and immediately causes inspection by the weight diagnosing component 21d to end. This is because the integrated diagnosing component 21f can conclude that the chain of successively connected packages M is a defective chain, regardless of the other inspection results, because a chain of successively connected packages M in which foreign matter has been detected or a chain of successively connected packages M in which a bag N1, N2, . . . , N6 that is abnormal in weight has been detected cannot be shipped. Further, when the integrated diagnosing component 21f receives signals indicating that no abnormality has been detected from both the weight diagnosing component 21d and the foreign matter inspecting component 21e, the integrated diagnosing component 21f diagnoses the chain of successively connected packages M as being a normal chain. Then, the integrated diagnosing component 21f sends the diagnostic results to the sorting mechanism 70.

Characteristics (1) The X-ray inspection apparatus 10 is equipped with the function of identifying the discrete package regions C1, C2, . . . , C6 from the X-ray image P and performing weight estimation with respect to each of the identified discrete package regions C1, C2, . . . , C6 and is capable of more accurately performing judgment of whether the chain of successively connected packages M is normal or defective. As the specific method by which the X-ray inspection apparatus 10 identifies the discrete package regions C1, C2, . . . , C6, there is employed a method where the X-ray inspection apparatus 10 measures the timings when the transverse seal sites S1 appear on the X-ray image P on the basis of the X-ray see-through image signals outputted from the X-ray line sensor 14. The transverse seal sites S1 are sites that configure the boundaries between the adjacent bags N1, N2, . . . , N6, so the X-ray inspection apparatus 10 is capable of identifying the positions of the discrete package regions C1, C2, . . . , C6 on the X-ray image P by identifying the positions of the transverse seal sites S1 that appear on the X-ray image P.

(2) The X-ray inspection apparatus 10 is capable of performing foreign matter inspection together with weight inspection. By performing weight inspection and foreign matter inspection with one apparatus in this manner, the footprint of the production line of the chain of successively connected packages M becomes reduced and costs for constructing the production line become reduced.

(3) In the X-ray inspection apparatus 10, even though plural types of inspection are executed, the inspections are managed by the integrated diagnosing component 21f such that when an abnormality is detected in any of the inspections, any remaining inspection is immediately caused to end. Thus, needless processing is eliminated and the processing burden of the X-ray inspection apparatus 10 is alleviated.

Modifications (1) In the region identification processing of the first embodiment, the X-ray inspection apparatus 10 identifies data corresponding to the transverse seal sites S1 from the time series data of the representative values of the concentration values and identifies the other data as data corresponding to the discrete package regions C1, C2, . . . , C6. However, when that is stably possible, the X-ray inspection apparatus 10 may also be configured to directly identify the data corresponding to the discrete package regions C1, C2, . . . , C6 without identifying the data corresponding to the transverse seal sites S1.

(2) The representative value decision processing by the region identifying component 21b of the first embodiment is not limited to the aforementioned method and may also be performed by the following method, for example.

First, the region identifying component 21b creates, on the basis of a data set of one group of concentration values (X-ray see-through image signals whose number corresponds to the number of the pixel sensors 14a outputted at substantially the same timing from the X-ray line sensor 14), a histogram of the concentration values. Then, the region identifying component 21b extracts a predetermined amount of data (e.g., 80% of the total amount) from the light side or the dark side of the concentration values in all of the data, uses the extracted data as a target to calculate an average value, and uses the average value as the representative value. When the region identifying component 21b extracts a predetermined amount of data from the light side of the concentration values, it becomes easier for the region identifying component 21b to confirm by using representative value the presence of targets (background, packaging material) that appear relatively light on the X-ray image P, and when the region identifying component 21b extracts a predetermined amount of data from the dark side of the concentration values, it becomes easier for the region identifying component 21b to confirm by using representative value the presence of targets (contents) that appear relatively dark on the X-ray image P.

(3) The representative value decision processing by the region identifying component 21b of the first embodiment is not limited to the aforementioned method and may also be performed by the following method, for example.

First, the region identifying component 21b creates, on the basis of a data set of one group of concentration values (X-ray see-through image signals whose number corresponds to the number of the pixel sensors 14a outputted at substantially the same timing from the X-ray line sensor 14), a histogram of the concentration values and then uses the peak value in the histogram as the representative value.

(4) In the weight estimation processing of the first embodiment, the X-ray inspection apparatus 10 is capable of avoiding weight estimation with respect to the region D corresponding to the background of the chain of successively connected packages M, for example, by setting beforehand a mask pattern that is applied to the discrete package regions C1, C2, . . . , C6. In this case, a reduction in error and simplification of processing are expected.

Second Embodiment

Next, the X-ray inspection apparatus 110 according to the second embodiment of the present invention will be described.

Figure 7:
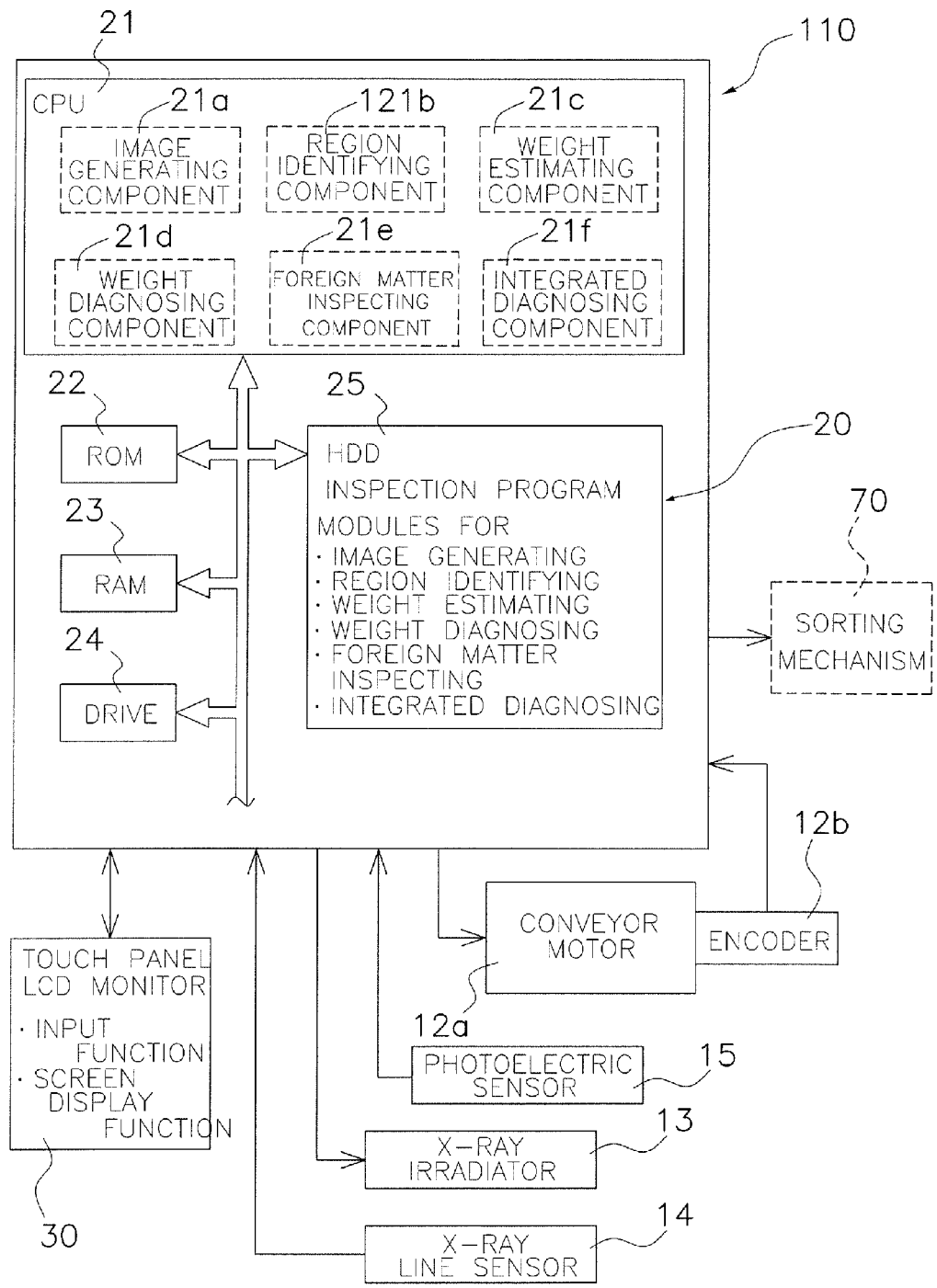
FIG. 7 is a block configuration diagram of a control computer according to a second embodiment of the present invention.

As shown in FIG. 7, the X-ray inspection apparatus 110 according to the second embodiment differs from the X-ray inspection apparatus 10 according to the first embodiment only in that the region identifying component 21b is replaced with a region identifying component 121b, and the X-ray inspection apparatus 110 is the same as the X-ray inspection apparatus 10 in all other respects. That is, the X-ray inspection apparatus 110 is an apparatus where the region identifying module stored in the HDD 25 of the control computer 20 of the X-ray inspection apparatus 10 is replaced with a different region identifying module. Consequently, below, only details of the region identification processing according to the second embodiment will be described, and all other configurations and operations of the X-ray inspection apparatus 110 will be regarded as being the same as those of the first embodiment and will not be described. Further, below, like the first embodiment, a case where the chain of successively connected packages M serves as the object of inspection will be taken as an example and described.

Region Identifying Component

First, the region identifying component 121b administers binary processing with respect to the X-ray image P that has been generated by the image generating component 21a and identifies the regions B1 representing the transverse seal sites S1 of the chain of successively connected packages M from the X-ray image P.

In the binary processing, it is checked whether or not the concentration values of the X-rays corresponding to each of the pixels that configure the X-ray image P fall within a predetermined range. Then, in accordance with the results of the checking, a value of either "0" or "1" is allocated to each pixel.

Figure 8:
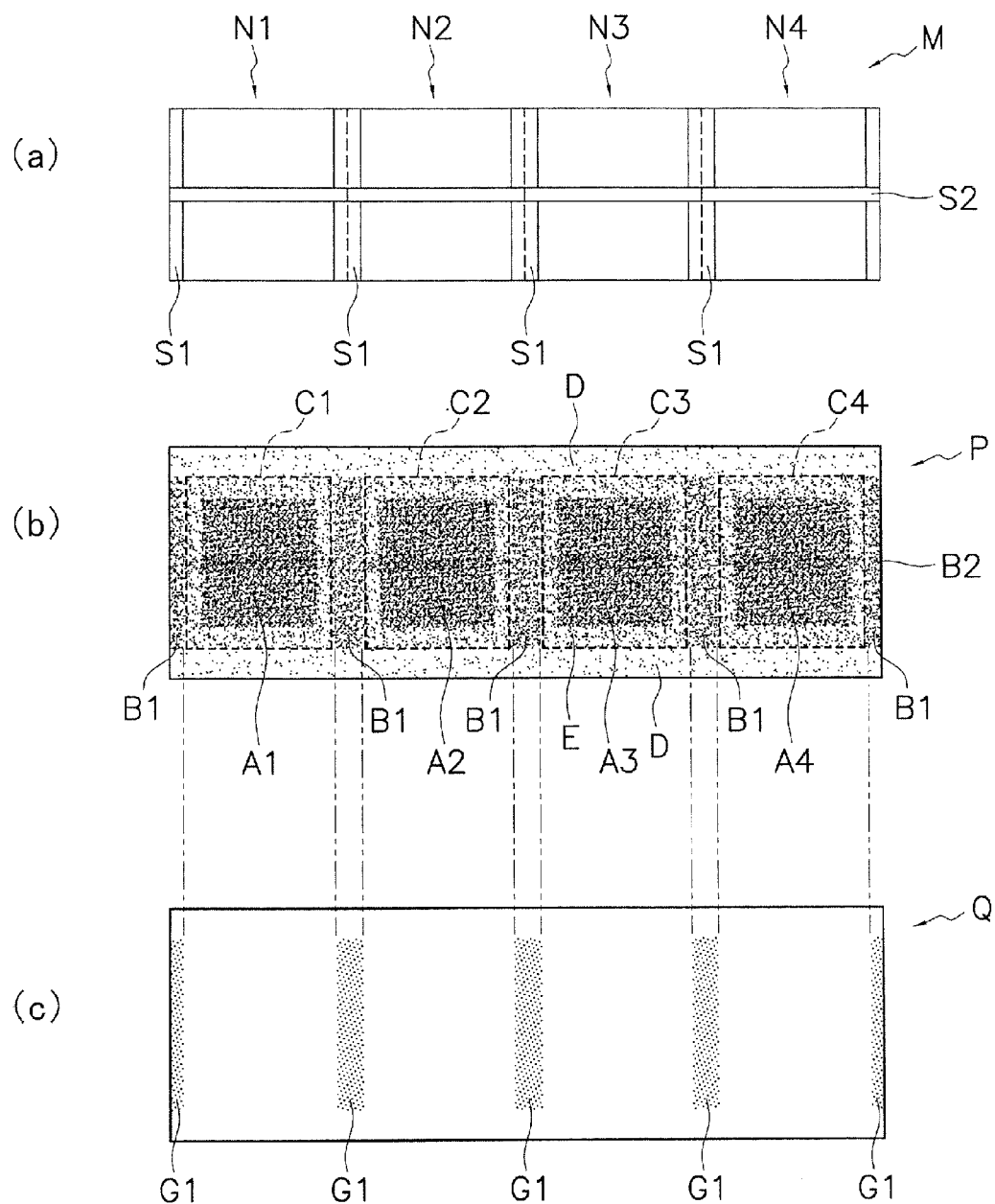
FIG. 8(a) is a diagram showing a chain of successively connected packages.
FIG. 8(b) is a diagram showing an X-ray image of the chain of successively connected packages.
FIG. 8(c) is a diagram showing a binary image of the chain of successively connected packages according to the second embodiment.

FIG. 8(c) shows a binary image Q after binary processing has been administered with respect to the X-ray image P shown in FIG. 8(b). Regions G1 that appear black on the binary image Q are regions corresponding to the transverse seal sites S1.

Next, the region identifying component 121b overlays the binary image Q on the X-ray image P and extracts the regions underlying the regions G1 on the X-ray image P as the regions B1 corresponding to the transverse seal sites S1. Then, the region identifying component 121b identifies the regions sandwiched between the regions B1 and the regions B1 as the discrete package regions C1, C2, . . . , C6. The discrete package regions C1, C2, . . . , C6 identified in the second embodiment are regions where the region D corresponding to the background of the chain of successively connected packages M is excluded from the discrete package regions C1, C2, . . . , C6 identified in the first embodiment.

Characteristics

The X-ray inspection apparatus 110 is equipped with the function of identifying the discrete package regions C1, C2, . . . , C6 from the X-ray image P and performing weight estimation with respect to each of the identified discrete package regions C1, C2, . . . , C6 and is capable of more accurately performing judgment of whether the chain of successively connected packages M is normal or defective. As the specific method by which the X-ray inspection apparatus 110 identifies the discrete package regions C1, C2, . . . , C6, there is employed a method where the X-ray inspection apparatus 110 administers image processing with respect to the X-ray image P.

Modifications (1) In the region identification processing of the second embodiment, binary processing is employed in order to extract the discrete package regions C1, C2, . . . , C6 from the X-ray image P. However, it is also possible to employ another form of image processing instead of, or in addition to, binary processing.

(2) In the region identification processing of the second embodiment, first, the X-ray inspection apparatus 110 extracts the regions B1 corresponding to the transverse seal sites S1 from the X-ray image P and extracts the discrete package regions C1, C2, . . . , C6 from the remaining region excluding the regions B1. However, when that is stably possible, the X-ray inspection apparatus 110 may also be configured to directly extract, as the discrete package regions C1, C2, . . . , C6, the regions A1, A2, . . . , A6 corresponding to the contents without extracting the regions B1.

Third Embodiment

Next, the X-ray inspection apparatus 210 according to the third embodiment of the present invention will be described.

Figure 9:
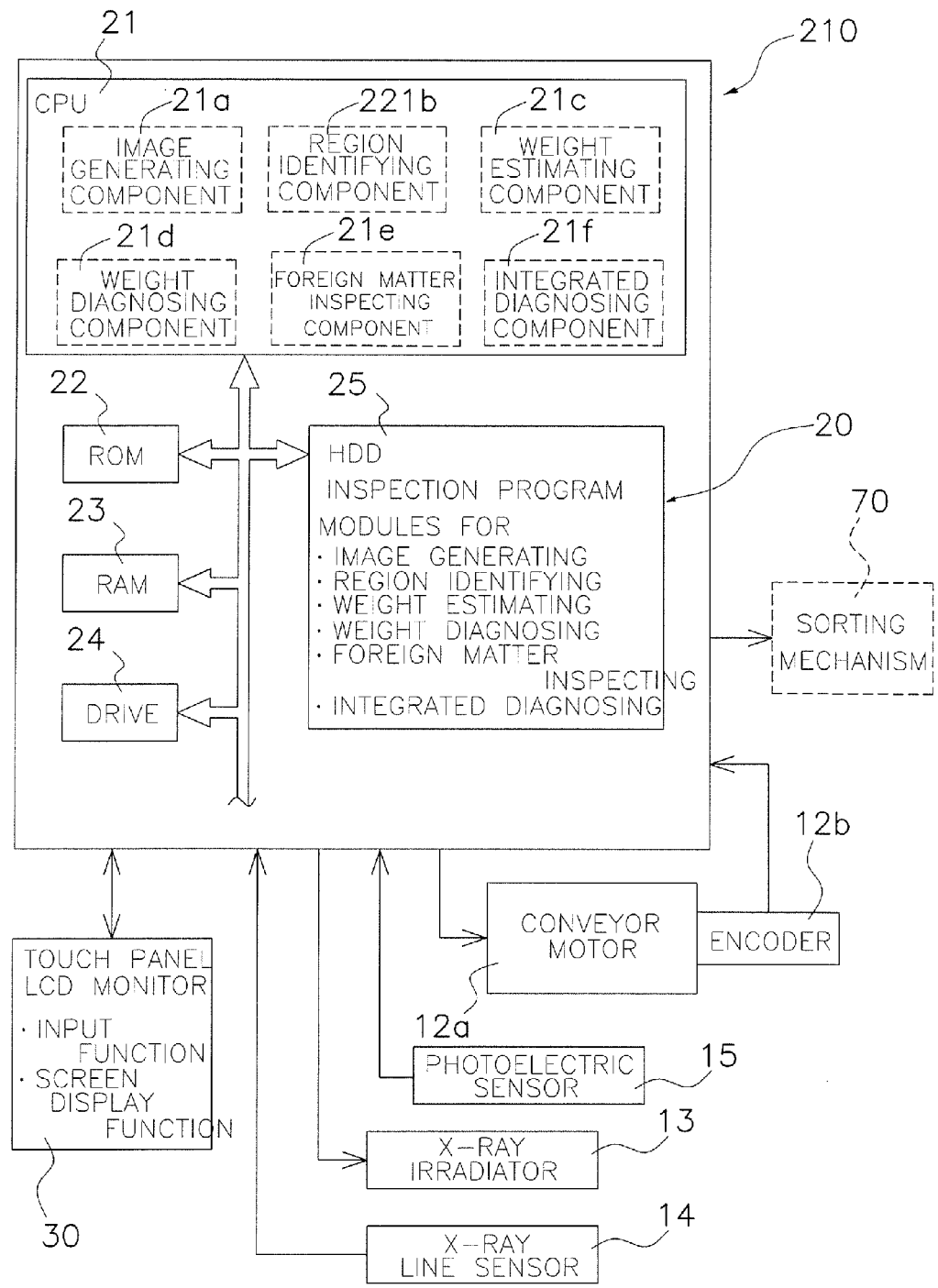
FIG. 9 is a block configuration diagram of a control computer according to a third embodiment of the present invention.

As shown in FIG. 9, the X-ray inspection apparatus 210 according to the third embodiment differs from the X-ray inspection apparatus 10 according to the first embodiment only in that the region identifying component 21b is replaced with a region identifying component 221b, and the X-ray inspection apparatus 210 is the same as the X-ray inspection apparatus 10 in all other respects. That is, the X-ray inspection apparatus 210 is an apparatus where the region identifying module stored in the HDD 25 of the control computer 20 of the X-ray inspection apparatus 10 is replaced with a different region identifying module. Consequently, below, only details of the region identification processing according to the third embodiment will be described, and all other configurations and operations of the X-ray inspection apparatus 210 will be regarded as being the same as those of the first embodiment and will not be described. Further, below, like the first embodiment, a case where the chain of successively connected packages M serves as the object of inspection will be taken as an example and described.

Region Identifying Component

In the HDD 25, a value representing a length L1 of each of the bags N1, N2, . . . , N6 is stored beforehand. The length L1 is based on the conveyance direction of the conveyor 12.

Figure 10:
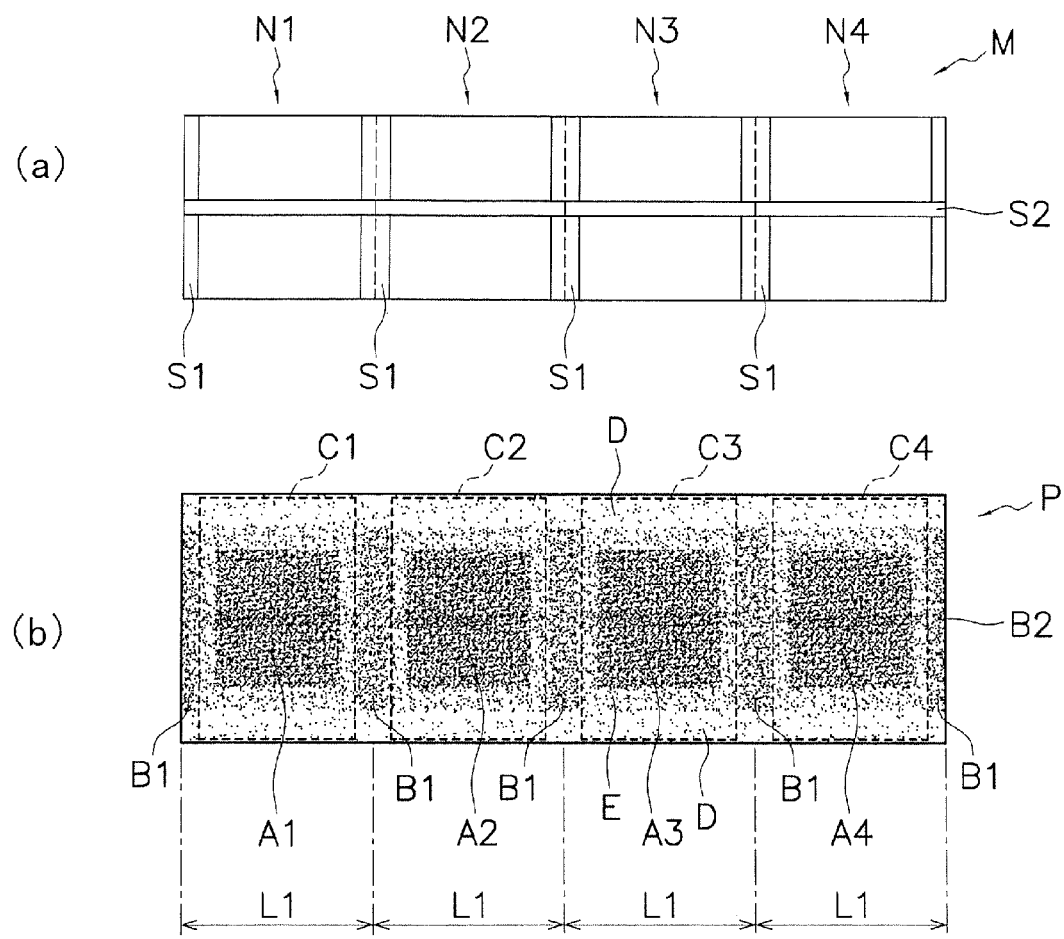
FIG. 10(a) is a diagram showing a chain of successively connected packages.
FIG. 10(b) is a diagram showing an X-ray image of the chain of successively connected packages according to the third embodiment.

The region identifying component 221b references the length L1 that the HDD 25 holds, sections the X-ray image P that has been generated by the image generating component 21a in the conveyance direction of the conveyor 12 per length L1, and identifies each of the sectioned regions as the discrete package regions C1, C2, . . . , C6 (see FIG. 10(b)).

Characteristics

The X-ray inspection apparatus 210 is equipped with the function of identifying the discrete package regions C1, C2, . . . , C6 from the X-ray image P and performing weight estimation with respect to each of the identified discrete package regions C1, C2, . . . , C6 and is capable of more accurately performing judgment of whether the chain of successively connected packages M is normal or defective. As the specific method by which the X-ray inspection apparatus 210 identifies the discrete package regions C1, C2, . . . , C6, there is employed a method where the X-ray inspection apparatus 210 calculates the discrete package regions C1, C2, . . . , C6 on the basis of an inspection parameter (the length L1 of each of the bags N1, N2, . . . , N6) stored in the HDD 25 beforehand.

Modifications (1) In the third embodiment, the length L1 of each of the bags N1, N2, . . . , N6 is stored in the HDD 25 as an inspection parameter for identifying the discrete package regions C1, C2, . . . , C6. However, the inspection parameter for identifying the discrete package regions C1, C2, . . . , C6 is not limited to this. For example, the X-ray inspection apparatus 210 may also be configured to store the number of the bags N1, N2, . . . , N6 included in the chain of successively connected packages M and to divide the X-ray image P showing the chain of successively connected packages M into the number of the bags N1, N2, . . . , N6 equally in the longitudinal direction of the chain of successively connected packages M. Further, the X-ray inspection apparatus 210 may also be configured to store the timing when each of the bags N1, N2, . . . , N6 passes through the X ray irradiated range X and to regard, as the discrete package regions C1, C2, . . . , C6, the regions on the X-ray image P based on the X-ray see-through image signals that have been acquired at those timings.

(2) In the region identification processing of the third embodiment, it is also possible to configure the X-ray inspection apparatus 210 such that the regions B1 corresponding to the transverse seal sites S1 and the region D corresponding to the background of the chain of successively connected packages M are not included in the discrete package regions C1, C2, . . . , C6, for example, by setting beforehand a mask pattern that is applied to the X-ray image P. In this case, a reduction in error and simplification of processing are expected.

Fourth Embodiment

Next, the X-ray inspection apparatus 310 according to the fourth embodiment of the present invention will be described.

Figure 11:
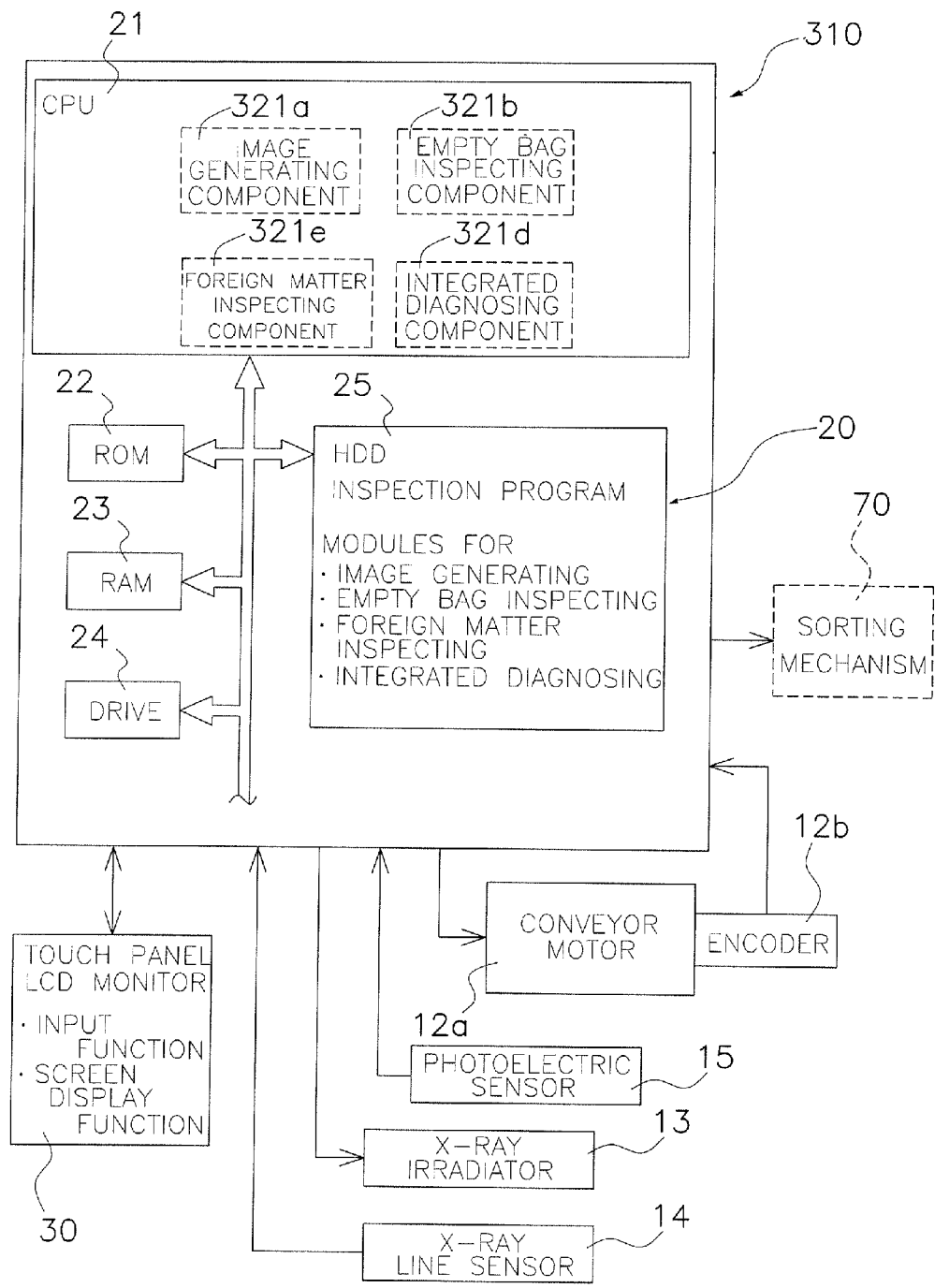
FIG. 11 is a block configuration diagram of a control computer according to a fourth embodiment of the present invention.

As shown in FIG. 11, the X-ray inspection apparatus 310 according to the fourth embodiment differs from the X-ray inspection apparatus 10 according to the first embodiment only in that an image generating component 321a, an empty bag inspecting component 321b, a foreign matter inspecting component 321c and an integrated diagnosing component 321d are present instead of the image generating component 21a, the region identifying component 21b, the weight estimating component 21c, the weight diagnosing component 21*d*, the foreign matter inspecting component 21*e* and the integrated diagnosing component 21*f*, and the X-ray inspection apparatus 310 is the same as the X-ray inspection apparatus 10 in all other respects. That is, the X-ray inspection apparatus 310 is an apparatus where the inspection program stored in the HDD 25 of the control computer 20 of the X-ray inspection apparatus 10 is replaced with a different inspection program. Consequently, below, only details of judgment processing of whether products are normal or defective by the control computer 20 according to the fourth embodiment will be described, and all other configurations and operations of the X-ray inspection apparatus 310 will be regarded as being the same as those of the first embodiment and will not be described.

Judgment of Whether Products are Normal or Defective by Control Computer

In the HDD 25 of the control computer 20, there is stored an inspection program that includes an image generating module, an empty bag inspecting module, a foreign matter inspecting module and an integrated diagnosing module. By reading and executing these program modules, the CPU 21 of the control computer 20 operates as the image generating component 321*a*, the empty bag inspecting component 321*b*, the foreign matter inspecting component 321*c* and the integrated diagnosing component 321*d* (see FIG. 11).

The image generating component 321*a* generates an X-ray image of the products G on the basis of the X-ray see-through image signals outputted from the X-ray line sensor 14.

The empty bag inspecting function resulting from the empty bag inspecting component 321*b* is a function that is used only when the products G that become objects of inspection are a chain of successively connected packages, and when the products G that become objects of inspection are not a chain of successively connected packages, the empty bag inspecting function is set to OFF by the operator. When the empty bag inspecting function is set to ON, the empty bag inspecting component 321*b* inspects whether or not an empty bag is included in the products G that are a chain of successively connected packages. When even one empty bag is present in the products G, the empty bag inspecting component 321*b* judges that product G to be abnormal.

The foreign matter inspecting component 321*c* inspects whether or not foreign matter is included in the products G When foreign matter is included, the foreign matter inspecting component 321*c* judges that product G to be abnormal.

The integrated diagnosing component 321*d* diagnoses a product G in which an abnormality has been detected by at least one of the empty bag inspecting component 321*b* and the foreign matter inspecting component 321*c* as being a defective product and diagnoses a product G in which no abnormality has been detected by either the empty bag inspecting component 321*b* or the foreign matter inspecting component 321*c* as being a normal product. The operator may also add a new inspecting module so that it is also possible for the integrated diagnosing component 321*d* to perform other inspection with respect to the products G. In this case, the integrated diagnosing component 321*d* diagnoses only a product G that has been judged to be normal in all of the inspections as being a normal product.

The diagnostic results of the integrated diagnosing component 321*d* are sent to the sorting mechanism 70. Then, the sorting mechanism 70 judges whether it should sort the products G onto the regular line conveyor 80 or the defective product storage conveyor 90 on the basis of the diagnostic results.

Below, details of the operation of the image generating component 321*a*, the empty bag inspecting component 321*b*, the foreign matter inspecting component 321*c* and the integrated diagnosing component 321*d* will be described.

Image Generating Component

The image generating component 321*a* acquires, in fine time intervals, the X-ray see-through image signals outputted from each of the pixel sensors 14*a* of the X-ray line sensor 14 when the products G pass through the fan-shaped X-ray irradiated range X (see FIG. 2) and generates an X-ray image of the products G on the basis of these X-ray see-through image signals. The timings when the products G pass through the fan-shaped X-ray irradiated range X are judged by signals from the photoelectric sensor 15. That is, the image generating component 321*a* generates an X-ray image showing the products G by joining together, in a matrix in a time series, data per fine time interval relating to the lightness of the X-rays obtained from each of the pixel sensors 14*a* of the X-ray line sensor 14.

Below, a case where a chain of successively connected packages M shown in FIG. 12(*a*) serves as the object of inspection will be taken as an example and described. The chain of successively connected packages M includes six bags N1, N2, . . . , N6 that are successively connected in order in a chain, and the bags N1, N2, . . . , N6 are manufactured such that they all have the same shape. The chain of successively connected packages M is conveyed by the conveyor 12 such that the bag N1 is at the front and the bag N6 is at the rear. Each of the bags N1, N2, . . . , N6 is a so-called pillow bag. Transverse seal sites S1 are formed on both ends of each of the bags N1, N2, . . . , N6 in the conveyance direction of the conveyor 12, and a vertical seal site S2 that extends in the conveyance direction is formed on the surface of each of the bags N1, N2, . . . , N6 that faces the conveyance surface of the conveyor 12. That is, the chain of successively connected packages M is a single long and narrow bag overall in which plural spaces corresponding to each of the bags N1, N2, . . . , N6 are formed by the transverse seal sites S1 administered at predetermined intervals in the longitudinal direction of the chain of successively connected packages M. Additionally, contents are packaged in the spaces inside the bags N1, N2, . . . , N6. Further, the transverse seal site 51 on the rear side of each preceding bag and the transverse seal site S1 on the front side of each following bag are integrally heat-sealed and formed, and in the center thereof, there is formed a perforation that runs in the short direction and enables both bags to be separated.

Figure 12:
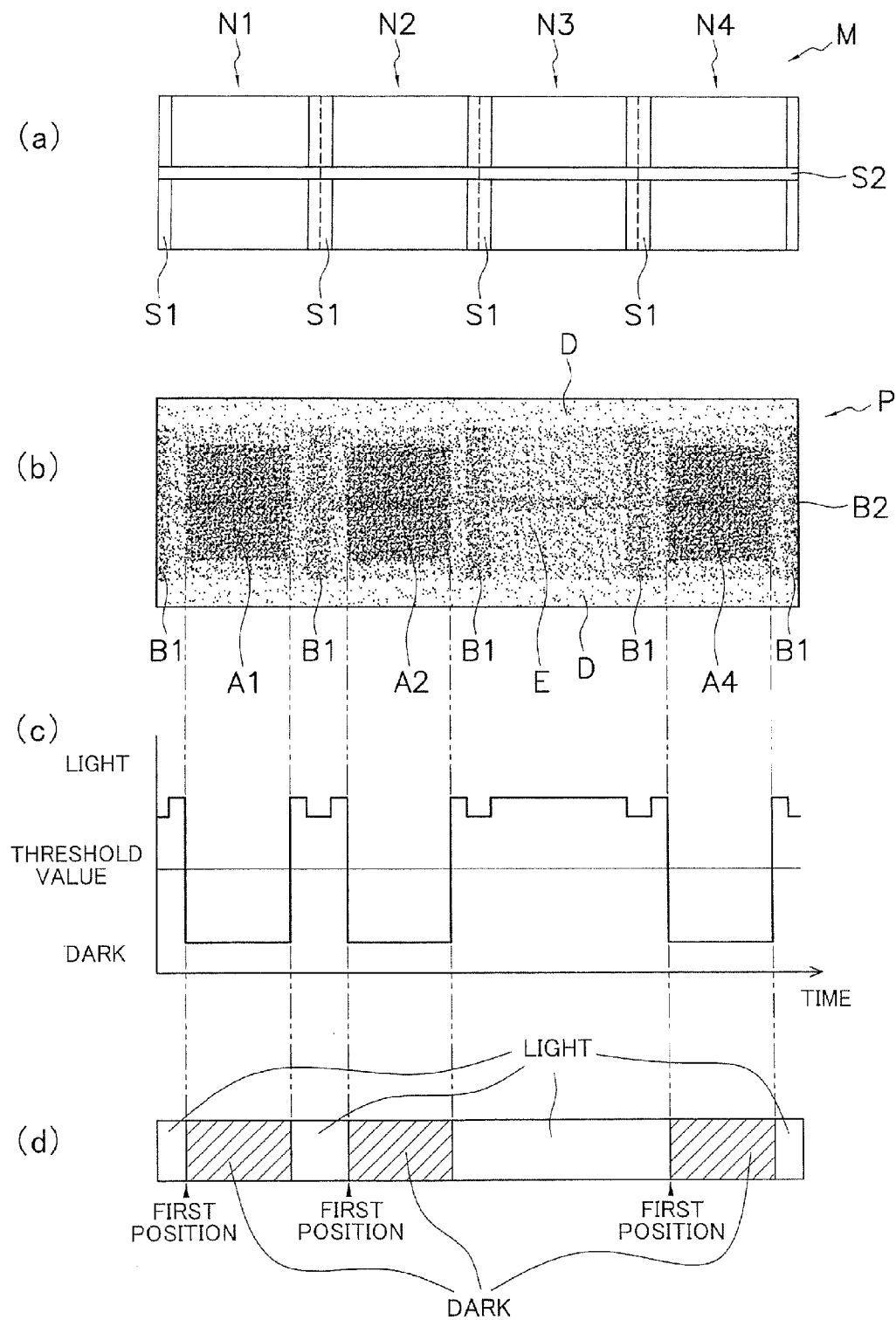
FIG. 12(a) is a diagram showing a chain of successively connected packages.
FIG. 12(b) is a diagram showing an X-ray image of the chain of successively connected packages.
FIG. 12(c) is a diagram showing the result of representative value decision processing.
FIG. 12(d) is a diagram showing the result of light/dark determination processing according to the fourth embodiment.

FIG. 12(*b*) shows an X-ray image P of the chain of successively connected packages M shown in FIG. 12(*a*). It will be noted that, for the sake of brevity, FIG. 12(*a*) to FIG. 12(*d*) show only the bags N1 to N4 of the entire chain of successively connected packages M. On the X-ray image P, regions A1, A2 and A4 that appear the darkest represent the contents inside the bags N1, N2 and N4 respectively, regions B1 represent the transverse seal sites S1, and a region B2 represents the vertical seal site S2. A region D that appears the lightest represents the background of the chain of successively connected packages M, and regions E that appear lighter than the regions B1 and B2 and darker than the region D represent vacant portions of the bags N1 to N4 where there are no contents. It is thought that the reason why the regions B1 corresponding to the transverse seal sites S1 appear darker on the X-ray image P than the regions E corresponding to sites that are not sealed, even though both regions are sites where the same number of layers of packaging material overlap, is because the density of the transverse seal sites S1 is higher because of heat shrinkage than that of sites that are not sealed. Further, when processing is administered to the seal sites S1 and S2 such that they become jagged, the seal sites S1 and S2 appear darker on the X-ray image P because of overlapping of the packaging material in comparison to when this processing is not administered.

Empty Bag Inspecting Component

Like the image generating component 321a, the empty bag inspecting component 321b acquires, in fine time intervals, the X-ray see-through image signals from each of the pixel sensors 14a of the X-ray line sensor 14. Additionally, the empty bag inspecting component 321b calculates an average value of concentration values of the X-rays that correspond to the number of the pixel sensors 14a and have been outputted at the same timing from the numerous pixel sensors 14a and uses the calculated value as a representative value of the concentration values of the X-rays in that timing. Additionally, the empty bag inspecting component 321b compares the representative value with a threshold value, regards a case where the representative value exceeds the threshold value as a "light state", and regards a case where the representative value falls below the threshold value as a "dark state". It will be noted that, as the threshold value that is used in this light/dark determination processing, a value with which the time of passage of contents and the time of non-passage of contents can be precisely distinguished is set beforehand. The empty bag inspecting component 321b repeats the representative value decision processing and the light/dark determination processing each time it receives a data set of one group of concentration values (X-ray see-through image signals whose number corresponds to the number of the pixel sensors 14a outputted at substantially the same timing).

FIG. 12(c) shows time series data of the representative values calculated on the basis of the X-ray see-through image signals when the bags N1 to N4 have passed through the X-ray irradiated range X. In this case, the light/dark determination processing results in what is shown in FIG. 12(d).

Next, the empty bag inspecting component 321b counts the number of times that positions (in FIG. 12(d), positions indicated by black triangle marks) at which light/dark state switches from the light state to the dark state emerge on the time series data of results of the light/dark determination processing whose target is the entire chain of successively connected packages M. Switching from the light state to the dark state means that the front of a mass of contents has passed the X-ray irradiated range X. That is, the number of times that light/dark state switches from the light state to the dark state means the number of masses of contents. Consequently, when the number of times that light/dark state switches from the light state to the dark state and the number of bags (in the present example, six) that are normally to be included in the chain of successively connected packages M do not match, it is possible to judge that an empty bag is included in the chain of successively connected packages M. Thus, when these numbers do not match, the empty bag inspecting component 321b judges the chain of successively connected packages M to be abnormal, and when these numbers match, the empty bag inspecting component 321b judges the chain of successively connected packages M to be normal.

Foreign Matter Inspecting Component

The foreign matter inspecting component 321c detects foreign matter included in the chain of successively connected packages M by administering image processing with respect to the X-ray image P of the chain of successively connected packages M that has been generated by the image generating component 321a. In this foreign matter inspection, binary processing is executed. That is, when a region that appears darker than a threshold value set beforehand is present on the X-ray image P of the chain of successively connected packages M, the foreign matter inspecting component 321c judges that foreign matter is mixed into the chain of successively connected packages M and judges the chain of successively connected packages M to be abnormal.

Further, the foreign matter inspecting component 321c is also capable of setting a mask on the X-ray image P. The mask is, for example, set with respect to the regions B1 corresponding to the transverse seal sites S1 of the chain of successively connected packages M and the region D corresponding to the background.

Integrated Diagnosing Component

When the empty bag inspecting component 321b and the foreign matter inspecting component 321c judge the chain of successively connected packages M to be abnormal, they immediately send signals indicating this to the integrated diagnosing component 321d. When the integrated diagnosing component 321d receives this signal from the empty bag inspecting component 321b, the integrated diagnosing component 321d diagnoses the chain of successively connected packages M as being a defective chain and immediately causes inspection by the foreign matter inspecting component 321c to end. When the integrated diagnosing component 321d receives this signal from the foreign matter inspecting component 321c, the integrated diagnosing component 321d diagnoses the chain of successively connected packages M as being a defective chain and immediately causes inspection by the empty bag inspecting component 321b to end. This is because the integrated diagnosing component 321d can conclude that the chain of successively connected packages M is a defective chain, regardless of the other inspection results, because a chain of successively connected packages M in which foreign matter has been detected or a chain of successively connected packages M in which an empty bag has been detected cannot be shipped. Further, when the integrated diagnosing component 321d receives signals indicating that no abnormality has been detected from both the empty bag inspecting component 321b and the foreign matter inspecting component 321c, the integrated diagnosing component 321d diagnoses the chain of successively connected packages M as being a normal chain. Then, the integrated diagnosing component 321d sends the diagnostic results to the sorting mechanism 70.

Characteristics (1) The X-ray inspection apparatus 310 is equipped with the function of inspecting whether or not an empty bag is included in the chain of successively connected packages M and is capable of more accurately performing judgment of whether the chain of successively connected packages M is normal or defective. Specifically, the X-ray inspection apparatus 310 judges the number of masses of contents of the chain of successively connected packages M indirectly by judging the number of times that light/dark state has switched from the light state to the dark state on the basis of the X-ray see-through image signals acquired in fine time intervals from each of the pixel sensors 14a of the X-ray line sensor 14. That is, the X-ray inspection apparatus 310 judges the presence of an empty bag by an emergent pattern of data corresponding to the light state and the dark state on the time series data of the light/dark determination processing results.

(2) The X-ray inspection apparatus 310 is capable of performing foreign matter inspection together with empty bag inspection. By performing foreign matter inspection and empty bag inspection with one apparatus in this manner, the footprint of the production line of the chain of successively connected packages M becomes reduced and costs for constructing the production line become reduced.

(3) In the X-ray inspection apparatus 310, even though plural types of inspection are executed, the inspections are managed by the integrated diagnosing component 321d such that when an abnormality is detected in any of the inspections, any remaining inspection is immediately caused to end. Thus, needless processing is eliminated and the processing burden of the X-ray inspection apparatus 310 is alleviated.

Modifications (1) In the empty bag inspection of the fourth embodiment, the X-ray inspection apparatus 310 counts the number of times that light/dark state switches from the light state to the dark state in order to count the number of masses of contents included in the chain of successively connected packages M. However, the X-ray inspection apparatus 310 may also count the number of times that light/dark state switches from the dark state to the light state. Switching from the light state to the dark state means that the end of a mass of contents has passed the X-ray irradiated range X. Consequently, the number of times that light/dark state switches from the dark state to the light state also means the number of masses of contents included in the chain of successively connected packages M.

Alternatively, the X-ray inspection apparatus 310 may also determine the number of masses of contents included in the chain of successively connected packages M by counting both the number of times that light/dark state switches from the light state to the dark state and the number of times that light/dark state switches from the dark state to the light state. This is because the combined value of the number of times that light/dark state switches from the light state to the dark state and the number of times that light/dark state switches from the light state to the dark state is a value that is determined depending on the number of masses of contents included in the chain of successively connected packages M (specifically, by dividing the combined value by 2) and indirectly means the number of masses of contents included in the chain of successively connected packages M.

(2) In the fourth embodiment, the X-ray inspection apparatus 310 performs empty bag inspection by comparing the number of times that light/dark state switches from the light state to the dark state with the number of bags that are normally to be included in the chain of successively connected packages M. However, the X-ray inspection apparatus 310 may also be configured to measure spans where the light state is continuous, judge the chain of successively connected packages M to be abnormal when the spans exceed a predetermined threshold value, and judge the chain of successively connected packages M to be normal when the spans fall below the predetermined threshold value.

The light state is a state that is judged on the basis of the X-rays that have passed mainly through the packaging material of the chain of successively connected packages M, and the dark state is a state that is judged on the basis of the X-rays that have passed mainly through the contents of the chain of successively connected packages M. That is, measuring spans where the light state is continuous means measuring the lengths, that are continuous in the conveyance direction, of portions of just the packaging material where there are no contents. Consequently, when this length exceeds the predetermined threshold value, the X-ray inspection apparatus 310 can presume the presence of an empty bag.

Further, as long as the empty bag inspection relates to processing in regard to the same chain of successively connected packages M, it is preferable for the empty bag inspection to be ended at a point in time when an abnormality in the spans is first detected. This is because, when it turns out that even one empty bag is included, the chain of successively connected packages M becomes a defective chain regardless of the results of processing thereafter.

It will be noted that the spans referred to here may be measured in terms of distance or may be measured in terms of time.

Further, the X-ray inspection apparatus 310 may also be configured such that, in a case where portions corresponding to each of the bags N1, N2, . . . , N6 on the time series data of the light/dark determination processing results are known beforehand, the X-ray inspection apparatus 310 measures spans where the dark state is continuous and which are included in data corresponding to each of the bags N1, N2, . . . , N6, judges the chain of successively connected packages M to be abnormal when the spans fall below a predetermined threshold value (including the case of zero), and judges the chain of successively connected packages M to be normal when the spans exceed the predetermined threshold value. It will be noted that a case where portions corresponding to each of the bags N1, N2, . . . , N6 on the time series data of the light/dark determination processing results are known beforehand is a case where the length of each of the bags N1, N2, . . . , N6 is known beforehand or a case where the total length of the chain of successively connected packages M and the number of bags included in the chain of successively connected packages M are known.

In this manner, it becomes possible for the X-ray inspection apparatus 310 to determine the presence of an empty bag by comparing the emergent pattern of at least one of the light state and the dark state with an expected emergent pattern.

(3) The representative value decision processing in the empty bag inspection of the fourth embodiment is not limited to the aforementioned method and may also be performed by the following method, for example.

First, the empty bag inspecting component 321b creates, on the basis of a data set of one group of concentration values (X-ray see-through image signals whose number corresponds to the number of the pixel sensors 14a outputted at the same timing from the X-ray line sensor 14), a histogram of the concentration values. Then, the empty bag inspecting component 321b extracts a predetermined amount of data (e.g., 80% of the total amount) from the light side or the dark side of the concentration values in all of the data, uses the extracted data as a target to calculate an average value, and uses the average value as the representative value. When the empty bag inspecting component 321b extracts a predetermined amount of data from the light side of the concentration values, it becomes easier for the empty bag inspecting component 321b to confirm the presence of targets (background, packaging material) that appear relatively light on the X-ray image P because of the representative value that is calculated, and when the empty bag inspecting component 321b extracts a predetermined amount of data from the dark side of the concentration values, it becomes easier for the empty bag inspecting component 321b to confirm the presence of targets (contents) that appear relatively dark on the X-ray image P.

It is also possible to combine this modification with the preceding modifications (1) and (2).

(4) The representative value decision processing in the empty bag inspection of the fourth embodiment is not limited to the aforementioned method and may also be performed by the following method, for example.

First, the empty bag inspecting component 321b creates, on the basis of a data set of one group of concentration values (X-ray see-through image signals whose number corresponds to the number of the pixel sensors 14a outputted at substantially the same timing from the X-ray line sensor 14), a histogram of the concentration values and then uses the peak value in the histogram as the representative value.

It is also possible to combine this modification with the preceding modifications (1) and (2).

Fifth Embodiment

Next, the X-ray inspection apparatus 410 according to the fifth embodiment of the present invention will be described.

Figure 13:
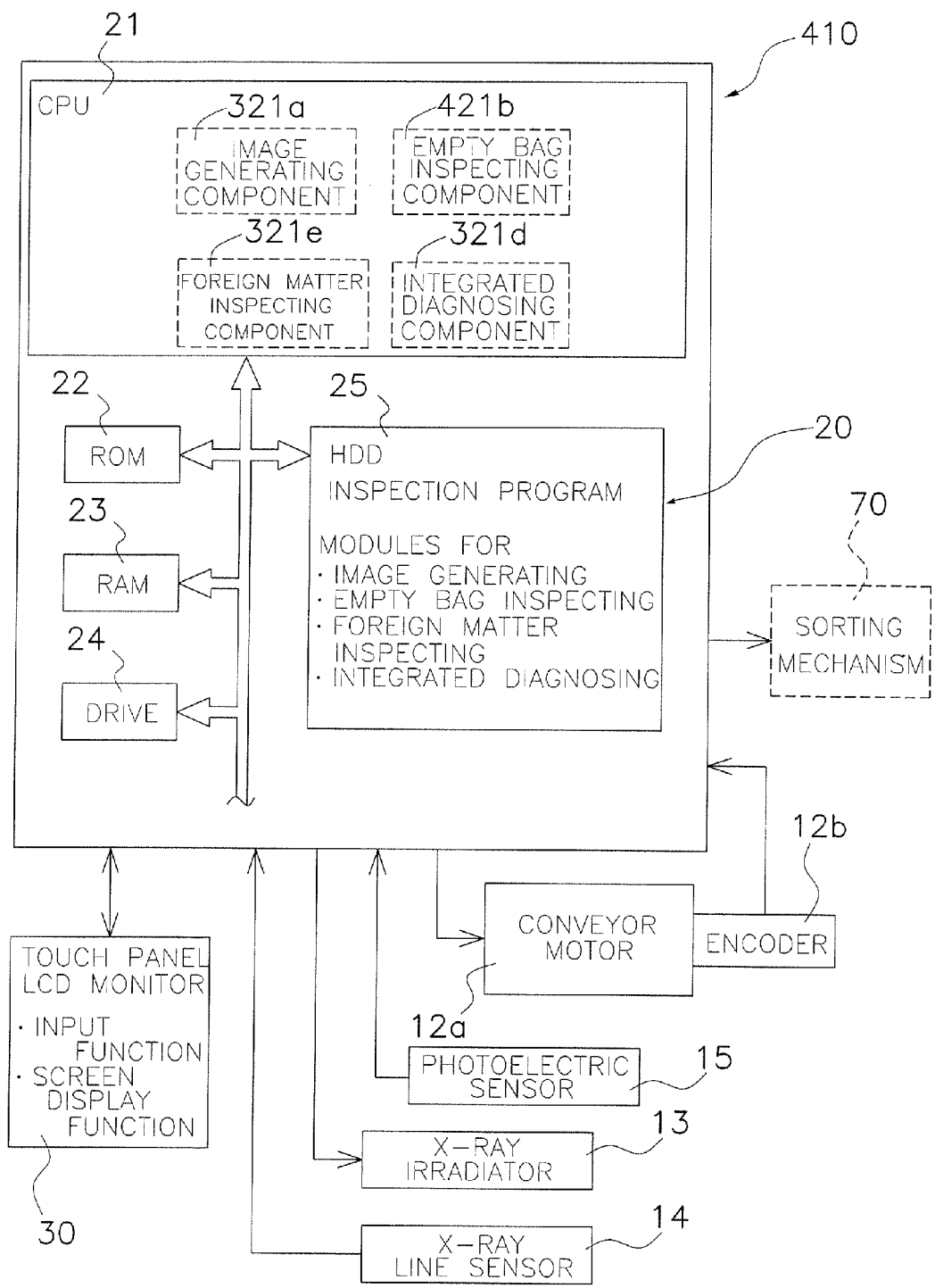
FIG. 13 is a block configuration diagram of a control computer according to a fifth embodiment of the present invention.

As shown in FIG. 13, the X-ray inspection apparatus 410 according to the fifth embodiment differs from the X-ray inspection apparatus 310 according to the fourth embodiment only in that the empty bag inspecting component 321b is replaced with an empty bag inspecting component 421b, and the X-ray inspection apparatus 410 is the same as the X-ray inspection apparatus 310 in all other respects. That is, the X-ray inspection apparatus 410 is an apparatus where the empty bag inspecting module stored in the HDD 25 of the control computer 20 of the X-ray inspection apparatus 310 is replaced with a different empty bag inspecting module. Consequently, below, only details of the empty bag inspection according to the fifth embodiment will be described, and all other configurations and operations of the X-ray inspection apparatus 410 will be regarded as being the same as those of the fourth embodiment and will not be described. Further, below, like the fourth embodiment, a case where the chain of successively connected packages M serves as the object of inspection will be taken as an example and described.

Empty Bag Inspecting Component

First, the empty bag inspecting component 421b administers binary processing with respect to the X-ray image P that has been generated by the image generating component 321a and separates the regions on the X-ray image P into regions representing contents and a region representing other than contents.

In the binary processing, the concentration values of the X-rays corresponding to each pixel configuring the X-ray image P are compared with a predetermined threshold value. Then, a value of either "0" or "1" is allocated to each pixel depending on the magnitude relation of those values. The threshold value used in the binary processing here is a value that is different from the threshold value used in the binary processing of foreign matter inspection.

Figure 14:
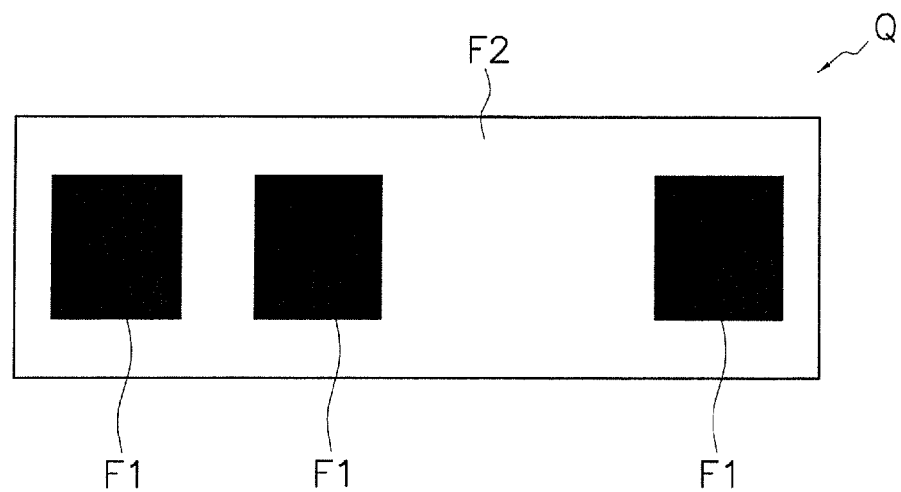
FIG. 14 is a diagram showing a binary image of a chain of successively connected packages according to a fifth embodiment.

FIG. 14 shows a binary image Q after binary processing has been administered with respect to the X-ray image P shown in FIG. 12(b). On the binary image Q, regions F1 that appear black correspond in principle to contents inside each of the bags N1, N2, . . . , N6, and a region F2 that appears white corresponds in principle to the portion of only the packaging material and the background of the chain of successively connected packages M.

Next, the empty bag inspecting component 421b counts the number of the regions F1. The number of the regions F1 means the number of masses of contents. Of all of the regions that appear black, only regions having an area within a predetermined range are counted. This is so that the empty bag inspecting component 421b does not count a region showing foreign matter or the like. Then, the empty bag inspecting component 421b compares the number of the regions F1 that has counted with the number of bags (in the present example, six) that are normally to be included in the chain of successively connected packages M, judges the chain of successively connected packages M to be abnormal when these numbers do not match, and judges the chain of successively connected packages M to be normal when these number match.

Characteristics

The X-ray inspection apparatus 410 is equipped with the function of inspecting whether or not an empty bag is included in the chain of successively connected packages M and is capable of more accurately performing judgment of whether the chain of successively connected packages M is normal or defective. Specifically, the X-ray inspection apparatus 410 judges the number of masses of contents of the chain of successively connected packages M by administering image processing with respect to the X-ray image P. Thus, the X-ray inspection apparatus 410 performs empty bag inspection while effectively utilizing the function that the foreign matter inspecting component 321c and the like use and with which it is inherently equipped.

Modifications (1) In the empty bag inspection of the fifth embodiment, binary processing is employed. However, it is also possible to employ another form of image processing instead of, or in addition to, binary processing.

(2) In the fifth embodiment, the X-ray inspection apparatus 410 performs empty bag inspection by comparing the number of the regions F1 that appear black on the binary image Q with the number of bags that are normally to be included in the chain of successively connected packages M. However, the X-ray inspection apparatus 410 may also be configured to measure the intervals between the plural regions F1 in the conveyance direction and judge the chain of successively connected packages M to be abnormal when the interval exceeds a predetermined threshold value and judge the chain of successively connected packages M to be normal when the interval falls below the predetermined threshold value.

Measuring the intervals between the plural regions F1 in the conveyance direction means measuring the distance between the masses of contents in the conveyance direction. Consequently, when this distance exceeds the predetermined threshold value, the X-ray inspection apparatus 410 can presume the presence of an empty bag.

Further, as long as the empty bag inspection relates to processing in regard to the same chain of successively connected packages M, it is preferable for the empty bag inspection to be ended at a point in time when an abnormality in the intervals is first detected. This is because, when it turns out that even one empty bag is included, the chain of successively connected packages M becomes a defective chain regardless of the results of processing thereafter.

Other Embodiments (1) The weight inspection of the first, second and third embodiments can also be used with respect to a chain of successively connected packages with a different configuration than that of the chain of successively connected packages M exemplified in the descriptions of the first, second and third embodiments. For example, a type of chain of successively connected packages called a strip pack may also be used. A strip pack is a chain of successively connected packages with a configuration where plural bags are adhered at predetermined intervals to a band-like, long and narrow tape (strip) to make it easy for consumers to remove the bags one at a time and make a purchase. Further, the bags N1, N2, . . . , N6 do not have to be pillow bags and may also be gusset bags or hem bags. Further, the chain of successively connected packages may also be a three-side seal type where the vertical seal site S2 is formed on one end portion in the short direction of the chain of successively connected packages M.

(2) In the first, second, third, fourth and fifth embodiments, each type of inspection is realized by the CPU 21 of the control computer 20. However, each type of inspection may also be realized by other software, hardware, or an arbitrary combination of these.

Further, processing pertaining to the control computer 20 may also be executed in an apparatus disposed separately from the X-ray apparatus 10, 110, 210, 310 and 410. For example, the various data may be sent from the control computer 20 to a separate computer via a network, and all or part of the processing may be executed in that separate computer.

(3) The system of image processing employed in the foreign matter inspection of the first, second, third, fourth and fifth embodiments is not limited to what has been described above; for example, instead of binary processing, trace detection processing may also be executed.

(4) The system of weight estimation processing employed in the weight inspection of the first, second and third embodiments is not limited to what has been described above; for example, correction processing that takes into consideration attenuation of the X-rays when the X-rays are transmitted through the air and the packaging material may also be added to the processing described above.

(5) The X-ray inspection apparatus 10, 110 and 210 may also include the function of judging that an empty bag is included in the chain of successively connected packages M and outputting indication of this when a weight value that has been estimated with respect to one of the discrete package regions C1, C2, . . . , C6 becomes zero or a value close to zero. Thus, a chain of successively connected packages in which an empty bag is present can be handled as a defective chain, in this X-ray inspection apparatus.

(6) The empty bag inspection of the fourth and fifth embodiments can also be used with respect to a chain of successively connected packages with a different configuration than that of the chain of successively connected packages M exemplified in the descriptions of the fourth and fifth embodiments. For example, a type of chain of successively connected packages called a strip pack may also be used. A strip pack is a chain of successively connected packages with a configuration where plural bags are adhered at predetermined intervals to a band-like, long and narrow tape (strip) to make it easy for consumers to remove the bags one at a time and make a purchase. Further, the bags N1, N2, . . . , N6 do not have to be pillow bags and may also be gusset bags or hem bags. Further, the chain of successively connected packages may also be a three-side seal type where the vertical seal site S2 is formed on one end portion in the short direction of the chain of successively connected packages M.

(7) Processing pertaining to each type of inspection that the control computer 20 executes in the first, second, third, fourth and fifth embodiments may be applied not only to X-ray inspection apparatus but also to inspection apparatus that use terahertz waves. In other words, the same processing as in the preceding embodiments can also be administered to terahertz waves that have been transmitted through products or inspection images based thereon.

The illustrated embodiments has the effect that it can more accurately perform judgment of whether a chain of successively connected packages is normal or defective and is useful as an inspection apparatus and particularly as an inspection apparatus that inspects a chain of successively connected packages including a plurality of discrete packages that are successively connected in a chain.

The invention claimed is:

1. An inspection apparatus that inspects a package group including a plurality of discrete packages that are successively connected in a chain, each of the discrete packages including seal sites and a contents site surrounded by corresponding ones of the seal sites, the inspection apparatus comprising:
　an irradiating component configured and arranged to irradiate inspection waves to the package group, the inspection waves being X-rays or terahertz waves;
　a light receiving component configured and arranged to receive the inspection waves from the irradiating component and transmitted through the package group;
　a generating component configured and arranged to generate an inspection image on the basis of the inspection waves that the light receiving component has received;
　a region identifying component configured to identify a plurality of discrete package regions corresponding to the discrete packages from the inspection image, identify seal regions corresponding to the seal sites of the discrete packages from the inspection image, identify a plurality of content regions corresponding to contents in the discrete package regions and identify the discrete package regions from the seal regions of the inspection image;
　a weight estimating component configured to estimate one or more weight values respectively corresponding to one or more of the discrete package regions; and
　a weight diagnosing component configured to diagnose the package group as being abnormal in weight when any of the weight values falls outside a predetermined range.

2. The inspection apparatus according to claim 1, wherein the region identifying component is configured to identify a plurality of the seal regions corresponding to the seal sites within the package group from the inspection image and to identify the content regions in regions other than the seal regions of the inspection image.

3. The inspection apparatus according to claim 1, wherein the region identifying component is configured to extract the discrete package regions by performing image processing with respect to the inspection image.

4. The inspection apparatus according to claim 1, wherein the region identifying component is configured to identify the discrete package regions from the inspection image on the basis of a parameter set beforehand.

5. The inspection apparatus according to claim 1, further comprising
　a foreign matter inspecting component configured to perform foreign matter inspection with respect to the package group on the basis of the inspection image.

6. The inspection apparatus according to claim 5, further comprising
　an integrated diagnosing component configured to diagnose the package group as being abnormal at least one of when the weight diagnosing component has diagnosed the package group as being abnormal in weight, and when the foreign matter inspecting component has diagnosed that foreign matter is mixed into at least one of the discrete packages of the package group.

7. The inspection apparatus according to claim 1, wherein the weight diagnosing component is configured to sequentially diagnose abnormality in each of the discrete packages of the package group as the weight estimating component completes estimation of the weight value of each of the discrete package regions, and the weight estimating component is configured to stop estimating the weight values of remaining ones of the discrete package regions at a point in time when one of the discrete packages of the package group is diagnosed by the weight diagnosing component as being abnormal in weight.

8. The inspection apparatus according to claim 1, wherein the weight diagnosing component is configured to determine whether or not an empty bag is included in the package group on the basis of the weight values.

9. The inspection apparatus according to claim 1, wherein the identifying component is configured to recognize a vacant region corresponding to an area where there is no content.

10. The inspection apparatus according to claim 1, further comprising a foreign matter inspecting component configured to identify the presence of foreign matter within the content in the discrete package regions.

* * * * *